United States Patent
Slack et al.

(10) Patent No.: US 8,546,085 B2
(45) Date of Patent: Oct. 1, 2013

(54) METHODS OF IDENTIFYING MODULATORS OF THE BITTER TASTE RECEPTOR TAS2R44

(75) Inventors: Jay Patrick Slack, Loveland, OH (US); Jenny Ellen Evans Pennimpede, Cincinnati, OH (US)

(73) Assignee: Givaudan SA, Vernier (CH)

( * ) Notice: Subject to any disclaimer, the term of this patent is extended or adjusted under 35 U.S.C. 154(b) by 0 days.

(21) Appl. No.: 12/996,670

(22) PCT Filed: Jun. 11, 2009

(86) PCT No.: PCT/CH2009/000199
§ 371 (c)(1),
(2), (4) Date: Dec. 7, 2010

(87) PCT Pub. No.: WO2009/149577
PCT Pub. Date: Dec. 17, 2009

(65) Prior Publication Data
US 2011/0311991 A1    Dec. 22, 2011

Related U.S. Application Data

(60) Provisional application No. 61/061,157, filed on Jun. 13, 2008.

(51) Int. Cl.
*G01N 33/567* (2006.01)

(52) U.S. Cl.
USPC .................. 435/7.1; 435/7.21; 436/501

(58) Field of Classification Search
None
See application file for complete search history.

(56) References Cited

U.S. PATENT DOCUMENTS

| 2006/0275765 | A1* | 12/2006 | Slack et al. | ............. 435/6 |
| 2007/0003679 | A1  | 1/2007  | Shimizu |  |

FOREIGN PATENT DOCUMENTS

| WO | 2008119195 A1 | 10/2008 |
| WO | 2008119196 A1 | 10/2008 |
| WO | 2008119197 A1 | 10/2008 |
| WO | 2009015504 A2 | 2/2009 |
| WO | 2009016374 A1 | 2/2009 |

OTHER PUBLICATIONS

Lindley, Other Sweeteners, Sweeteners and Sugar Alternatives in Food Technology, 2006, Blackwell Publishing Ltd, pp. 331-362.*
Ahern, Biochemical, Reagents Kits Offer Scientists Good Return on Investment, 1995, The Scientist, 9, pp. 1-7.*
XP002543470, Diterpenoid Sweeteners Synthesis and Sensory Evaluation of Stevioside Analogs with Improved, Organoleptic Properties, G.E. Dubois et al., Journal of Medicinal Chemistry, vol. 28, No. 1, 1985, pp. 93-38.
XP002543471, Masking Bitter Taste by Molecules, J.P. Ley, Chem. Percept., vol. 1, Feb. 2008, pp. 58-77.
Steviol Glycosides, Harriet Wallin, Chemical and Technical Assessment 63rd JECFA, FAO 2004.
Steviol Glycoside Biosynthesis, J.E. Brendle et al., Science Direct Phytochemistry 68 (2007) 1855-1863.
Highly Sweet Compounds of Plant Origin, Nam-Cheol Kim et al., Archives of Pharmacal Research, vol. 25, No. 6, pp. 725-746, 2002.

* cited by examiner

*Primary Examiner* — John Ulm
(74) *Attorney, Agent, or Firm* — Norris McLaughlin & Marcus PA

(57) ABSTRACT

Steviol glycosides have been discovered to bind the bitter taste receptor TAS2R44. Novel methods of identifying modulators and in particular inhibitors to the bitter taste of steviol glycosides and an inhibitor of steviol glycosides are provided.

24 Claims, No Drawings

METHODS OF IDENTIFYING MODULATORS OF THE BITTER TASTE RECEPTOR TAS2R44

This is an application filed under 35 USC 371 of PCT/CH2009/000199.

TECHNICAL FIELD

Provided are methods of identifying modulators of the bitter taste/aftertaste associated with steviol glycosides.

BACKGROUND

Steviol glycosides are found in the leaves of *Stevia rebaudiana* (Bertoni) Bertoni (Compositae), and/or *Rubus suavissimus* S. Lee (Rosaceae) and are responsible for the sweet taste of the leaves. A number of high potency sweeteners of plant origin are known and the major 20 structural types have been reviewed, for example, by Kim and Kinghorn (2002), Arch Pharm Res 25, 725-746. One subgroup of terpene high potency sweeteners are diterpene compounds, among which the so-called "steviol glycosides", also known as "ent-kaurene glycosides", form another subgroup.

Steviol glycosides range in sweetness from 40 to 300 times sweeter than sucrose. However, as with many high potency sweeteners, they also provide a bitter taste and/or off-note/aftertaste, and this limits their use in consumables. Methods that are able to identify agents that are able to modulate, and in particular to inhibit or mask, this bitter taste/aftertaste of steviol glycosides are therefore of interest.

Bitter taste is perceived via taste receptors, and a family of at least 25 functional bitter taste receptors (TAS2R or T2R) is known. Extensive deorphanization work has been done and many ligands have been published. However, none of these receptors has previously been shown to be activated by steviol glycosides.

SUMMARY OF THE INVENTION

It has been found that one of these receptors is activated by steviol glycosides.

In particular, there have been identified steviol glycosides as specific agonists of taste receptor type 2 member 44 (TAS2R44, also known as T2R44).

This finding allows the provision of methods that employ the identified TAS2R44 and its steviol glycoside agonists to identify agents that modulate the response of TAS2R44 to steviol glycosides, for example, antagonists (blockers, inhibitors or masking agents) of the steviol glycoside-dependent TAS2R44 activation. The methods therefore allow the identification of modulators including bitter masking or blocking agents for steviol glycosides, as was demonstrated for 4-(2,2,3-trimethyl-cyclopentyl)-butanoic acid, which was shown to inhibit the response of TAS2R44 to steviol glycosides, and to significantly reduce the bitter taste/aftertaste of steviol glycosides in human sensory evaluations.

Provided is the following:
(1) A method to identify an agent that modulates the taste of a steviol glycoside comprising:

(i) contacting cells that express a TAS2R44 bitter taste receptor that is able to be activated by a steviol glycoside in the presence of at least one agent; and
(ii) determining whether the at least one agent affects binding of said TAS2R44 bitter taste receptor to the one or more steviol glycoside,
or a functional response to the binding of said TAS2R44 bitter taste receptor to the one or more steviol glycoside,
with the proviso that the cells are not unmanipulated cells in their natural environment.
(2) The method described herein under item (1), wherein the one or more steviol glycoside is a steviol glycoside of formula F(I),

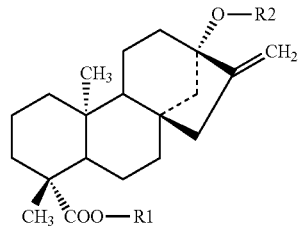

F(I)

wherein R1 and R2 are residues independently selected from the group consisting of H, beta-Glc, beta-Glc-beta-Glc(2->1), beta-Glc[beta-Glc(3->1)]-beta-Glc(2->1), beta-Glc-alpha-Rha(2->1), beta-Glc[beta-Glc(3->1)]-alpha-Rha(2->1), and beta-Glc[beta-Glc(3->1)]-alpha-Xyl(2->1).
(3) The method described herein under any one of items (1) to (2), wherein the TAS2R44 bitter taste receptor comprises one or more sequences selected from
a TAS2R4 bitter taste receptor substantially homologous to a polypeptide sequence selected from the group consisting of a SEQ ID NO:2 with a sequence identity of at least 90%;
a TAS2R44 bitter taste receptor which is encoded by a nucleotide sequence selected from the group consisting of
a nucleic acid substantially homologous to the nucleotide sequence of SEQ ID NO:1, as determined by sequence identity,
a nucleic acid substantially homologous to the nucleotide sequence of SEQ ID NO:1 as determined by hybridisation,
wherein the substantially homologous nucleic acid as determined by sequence identity has a sequence identity of at least 90%;
wherein the substantially homologous nucleic acid as determined by hybridization hybridizes under stringent hybridization conditions at a temperature of 42° C. in a solution of 50% formamide, 5×SSC, and 1% SDS, and washing at 65° C. in a solution of 0.2×SSC and 0.1% SDS;
wherein the nucleic acid optionally comprises SEQ ID NO:4 (HSV tag) at or near its end to form the C-terminus in the corresponding protein, and optionally comprises a membrane export tag, optionally selected from rat somatostatin (RSS) and rhodopsin, optionally selected from SEQ ID NO:3 (RSS tag), at or near its end to form the N terminus,
and wherein the TAS2R44 bitter taste receptor optionally comprises one or more tags optionally selected from TAS2R44 detection tag and membrane export tag.

The one or more tags of the TAS2R44 sequence include as a TAS2R44 detection tag SEQ ID NO:4 (HSV tag) present at or near the C-terminus of the resulting TAS2R44 protein; and as a membrane-export tag, includes the rat somatostatin (RSS) tag and the rhodopsin tag, for example, SEQ ID NO:3 (RSS), at or near the N terminus of the resulting TAS2R44 protein.

(4) The method described herein under any one of items (1) to (3), wherein the TAS2R44 bitter taste receptor comprises a conservative functional variant of the TAS2R44 bitter taste receptor that is able to be activated by one or more steviol glycoside.

(5) The method described herein under any one of items (1) to (4), wherein the cells also express a G-Protein, optionally a chimeric G-protein substantially homologous to Gaq-Gustducin, optionally the chimeric G-protein G alpha 16-gustducin 44.

(6) The method described herein under any one of items (1) to (5), wherein step (ii) comprises measuring a change in or caused by intracellular messengers.

(7) The method described herein under any one of items (1) to (6), comprising determining the functional response by measuring a change in an intracellular messenger selected from IP3 and calcium$^{2+}$.

(8) The method described herein under any one of items (1) to (7), wherein said cells are selected from the group consisting of bacterial cells, eucaryotic cells, yeast cells, insect cells, mammalian cells, amphibian cells, worm cells and combinations thereof.

(9) The method described herein under item (8), wherein the cell comprises a mammalian cell.

(10) The method described herein under item (9), wherein the cell comprises a mammalian cell selected from the group consisting of CHO, COS, HeLa, HEK-293 cells and combinations thereof.

(11) The method described herein under any one of items (1) to (10) wherein step (i) further comprises contacting the TAS2R44 bitter taste receptor with a test agent in presence of calcium, optionally in the form of calcium chloride.

(12) A kit comprising:
 (i) recombinant cells that express a TAS2R44 bitter taste receptor as defined herein under any one of items (1) to (4), and
 (ii) one or more steviol glycoside,
 for combined use to identify test agents as modulators of the taste of a steviol glycoside.

(13) A method of using the kit described in item (12) above, comprising:
 (i) growing recombinant cells that express the TAS2R44 bitter taste receptor as defined herein under any one of items (1) to (3),
 (ii) adding at least one test agent in the presence of one or more steviol glycoside, and
 (iii) determining a change in a functional response of the cells by comparing the response in presence and absence of the test agent,
 to identify test agents that modulate the taste of sucralose.

A suitable concentration of the steviol glycoside is selected to provide an easily measurable functional response, for example, without limitation, 0.005 to 100 millimolar.

(14) A method of identifying an agent that modulates the TAS2R44 bitter taste receptor as defined in any one of items (1) to (4) above, the method comprising:
 (i) measuring a parameter that changes in response to the steviol glycoside binding to the TAS2R44 bitter taste receptor, and
 (ii) determining a change of the parameter in response to a test agent, in comparison to a negative control and thereby identifying a modulator of the taste of the steviol glycoside.

(15) Method as described in item (14) above, wherein step (i) is performed by a method selected from the group consisting of fluorescence spectroscopy, NMR spectroscopy, measuring of one or more of absorbance, refractive index, hydrodynamic methods, chromatography, measuring solubility, biochemical methods, wherein the methods measure the properties of the TAS2R44 bitter taste receptor in a suitable environment selected from the group consisting of solution, bilayer membrane, attached to a solid phase, in a lipid monolayer, bound on a membrane, and in vesicles.

DETAILED DESCRIPTION

It has been discovered that steviol glycosides bind the bitter taste receptor, TAS2R44. This discovery allows the provision of novel methods of identifying modulators and in particular inhibitors to the bitter taste/aftertaste of steviol glycosides including, without limitation, rebaudioside A and stevioside. Accordingly, there has been identified an inhibitor able to inhibit the bitter taste of steviol glycosides, in particular, of stevioside and rebaudioside A. The chemical structure of stevioside glycosides is indicated below.

The term "steviol glycosides" refers to glycosides of the aglycone steviol. The term "steviol" means the diterpenoic compound hydroxy-ent-kaur-16-en-13-ol-19-oic acid. The chemical structure of steviol glycosides of formula (I) is indicated in the formula below.

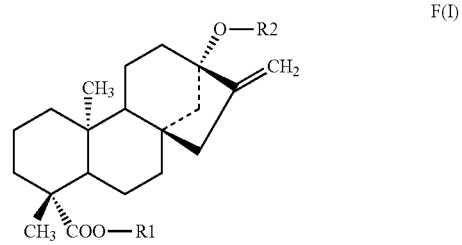

F(I)

R1 and R2 of F(I) may be independently selected from H, beta-Glc, beta-Glc-beta-Glc(2->1), beta-Glc[beta-Glc(3->1)]-beta-Glc(2->1), beta-Glc-alpha-Rha(2->1), beta-Glc[beta-Glc(3->1)]-alpha-Rha(2->1), beta-Glc[beta-Glc(3->1)]-alpha-Xyl(2->1).

Steviol glycosides as described herein include naturally-occurring compounds, for example, without limitation, those found in extracts of *Stevia rebaudiana* (Bertoni) Bertoni (Compositae), and/or *Rubus suavissimus* S. Lee (Rosaceae), and the many known derivatives, for example, without limitation, the steviol glycosides described in JP2131592, JP1254696, and U.S. Pat. No. 4,381,402. Further steviol glycosides and methods how to form them are described in EP1897951.

Examples of naturally occurring steviol glycosides include, without limitation, dulcoside A, rebaudioside A, rebaudioside B, rebaudioside C, rebaudioside D, rebaudioside E, rebaudioside F, rubusoside (desglucosylsstevioside), steviolbioside, steviol 13-O-beta-D-glucoside (steviolmonoside), 19-O-beta-glucopyranosyl-steviol, stevioside, suavioside A, suavioside B, suavioside G, suavioside H, suavioside I, and suavioside J. Some examples of these steviol glycosides and their chemical structure are indicated in the table below.

| Name | formula | R1 | R2 |
|---|---|---|---|
| dulcoside A | F (I) | beta-Glc | beta-Glc-alpha-Rha(2->1) |
| rebaudioside A | F (I) | beta-Glc | beta-Glc[beta-Glc(3->1)]-beta-Glc(2->1) |
| rebaudioside B | F (I) | H | beta-Glc[beta-Glc(3->1)]-beta-Glc(2->1) |
| rebaudioside C | F (I) | beta-Glc | beta-Glc[beta-Glc(3->1)]-alpha-Rha(2->1) |
| rebaudioside D | F (I) | beta-Glc-beta-Glc(2->1) | beta-Glc[beta-Glc(3->1)]-beta-Glc(2->1) |
| rebaudioside E | F (I) | beta-Glc-beta-Glc(2->1) | beta-Glc-beta-Glc(2->1) |
| rebaudioside F | F (I) | beta-Glc | beta-Glc[beta-Glc(3->1)]-alpha-Xyl(2->1) |
| steviolbioside | F (I) | H | beta-Glc-beta-Glc(2->1) |
| stevioside | F (I) | beta-Glc | beta-Glc-beta-Glc(2->1) |
| rubusoside | F(I) | beta-Glucose | beta-Glucose |
| steviol-13-O-beta-D-glucoside (steviolmonoside) | F(I) | H | beta-Glucose |

As an example, the structure of stevioside (R1=beta-Glc, R2=beta-Glc-beta-Glc(2->1)) is shown below.

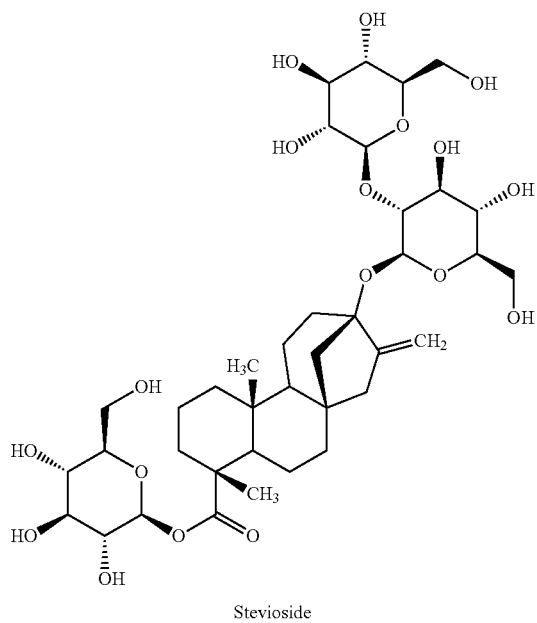 [SMILES: C=C1C[C@]23CCC4[C@](C)(CCC[C@@]4(C)C(=O)O[C@@H]4O[C@H](CO)[C@@H](O)[C@H](O)[C@H]4O)C2CC[C@@]1(O[C@@H]1O[C@H](CO)[C@@H](O)[C@H](O)[C@H]1O[C@@H]1O[C@H](CO)[C@@H](O)[C@H](O)[C@H]1O)C3]

Stevioside

Rebaudioside A differs from stevioside in R2, where a third glucose residue is present, with the glucose triplet being bound to steviol through the middle glucose unit (beta-Glc[beta-Glc(3->1)]-beta-Glc(2->1)).

If R1 or R2 of F(I) is a glycoside residue, this residue comprises up to 3 sugar units connected through glycosidic bonds, wherein at least one is beta-Glc and connects the residue to the steviol backbone (primary sugar unit). These remaining sugar units include, without limitation, Glucose (Glc), Rhamnose (Rha), Xylose (Xyl), Arabinose (Ara), Galactose (Gal), Mannose (Man), Fructose (Fm), Ribose (Rib), Fucose (Fuc), Glucosamine (GlcN), Galactosamine (GalN), Mannosamine (ManN), N-acetylglucosamine (GlcNAc), N-acetylgalactosamine (GalNAc), N-acetylmannosamine, (ManNAc), Glucuronic acid (GlcA), Galacturonic acid (GalA), Mannuronic acid (ManA), N-acetylneuraminic acid (NeuNAc), 3-deoxy-D-manno-2-octulosonic acid (Kdo).

In one embodiment of R1 or R2, the second or third residues (secondary residues) comprise at least one non-beta-Glc sugar unit optionally selected from alpha-Rha and alpha-Xyl.

In another embodiment, the primary beta-Glc is connected via a (3->1) bond to a secondary sugar unit selected from alpha-Rha and alpha-Xyl.

In yet another embodiment of R1 or R2, there are two sugar units and the primary beta-Glc is connected via a (3->1) bond to the secondary sugar unit selected from alpha-Rha and alpha-Xyl.

In still another embodiment of R1 or R2, the primary beta-Glc is connected via a (3->1) bond to a secondary beta-Glc, and connected via a (2->1) bond to a second secondary sugar unit selected from alpha-Rha and alpha-Xyl.

Steviol glycosides may be used in screening methods individually or as a mixture, they may be of natural origin and extracted or otherwise isolated, or chemically synthesized. For example, they may be used in form of a botanical extract, for example, an extract of plant leaves, including, without limitation, stevia extract. Stevia extract contains four major steviol glycosides, about 5-10% (w/w) stevioside, 2-4% (w/w) rebaudioside A 1-2% (w/w) rebaudioside C and 0.5-1% (w/w) dulcoside A, and smaller amounts of additional steviol glycosides.

The methods provided herein permit the identification of test agents that increase or decrease the effect of steviol glycosides on TAS2R44 (modulators). The methods may be in vivo or in vitro. Cells expressing TAS2R44, and optionally a G-protein, are contacted with test agents in combination with one or more steviol glycoside to determine the properties of said agents as steviol glycoside taste modulators, including but not limited to steviol glycoside bitterness blockers.

The effects of the test agents upon TAS2R44 can be measured by examining any suitable parameters of TAS2R44 binding, or an activated TAS2R44 functional response; any suitable assay detecting TAS2R44 receptor activity can be used, a number of examples are detailed below.

Receptor activation typically initiates subsequent intracellular events, for example, increases in second messengers, for example, IP3, which releases intracellular stores of calcium ions. Activation of some G-protein coupled receptors stimulates the formation of inositol triphosphate (IP3) through phospholipase C-mediated hydrolysis of phosphatidylinositol. IP3 in turn stimulates the release of intracellular calcium ion stores. Thus, a change in cytoplasmic calcium ion levels, or a change in second messenger levels such as IP3 can be used to determine G-protein coupled receptor activity.

The functional effects of the agent on the receptor and/or G-protein are determined by any suitable functional assay measuring the functional response, for example, an assay that measures changes in parameters of the transduction pathways such as intracellular $IP_3$ and $Ca^{2+}$, or by other G-protein specific assays such as labeling with GTPγS, according to techniques known in the art. Alternatively, binding assays may be used to determine the effect on steviol glycoside binding to TAS2R44. The identified agent can then be further tested for its activity as a modulator of steviol glycosides according to techniques known in the art, described without limitation herein below.

A functional response that can be used to identify a modulator comprises any physiological change that is affected by TAS2R44 activity; a variety of such changes is determined in different functional assays.

Such functional assays are well known in the art, for example, without limitation, assays that use recombinant cells or intact cells or tissues isolated from animals and that are based on measuring the concentration, activity, or change of a secondary messenger (including, for example, intracellular calcium (Ca2+), cAMP, cGMP, inositol phosphate (IP3), diacylglycerol/DAG, arachinoid acid, MAP kinase or tyrosine kinase), ion flux, phosphorylation levels, transcription levels, neurotransmitter levels, and assays based on GTP-binding, GTPase, adenylate cyclase, phospholipid-breakdown, diacylglycerol, inositol triphosphate, arachidonic acid release, PKC, kinase and transcriptional reporters. Some suitable assays are, for example, described in WO 01/18050. Various functional assays are exemplified herein-below; example 3 describes a fluorescent assay that detects calcium.

Receptor activation typically initiates subsequent intracellular events, for example, increases in second messengers, for example, $IP_3$, which releases intracellular stores of calcium ions. Activation of some G-protein coupled receptors stimulates the formation of inositol triphosphate ($IP_3$) through phospholipase C-mediated hydrolysis of phosphatidylinositol. $IP_3$ in turn stimulates the release of intracellular calcium ion stores. Thus, a change in cytoplasmic calcium ion levels, or a change in second messenger levels such as $IP_3$ can be used to determine G-protein coupled receptor activity. All functional assays may be performed with, for example, samples containing cells expressing the receptor on their surfaces or on isolated cell membrane fractions. Useful cells are described in more detail hereinunder. Also, for example, tissues from transgenic animals may be used.

To identify a modulator (which is not an agonist itself, e.g. an antagonist, inhibitor, or enhancer), samples with and without test agent both containing a steviol glycoside (agonist) are compared. For example, a control (with a steviol glycoside but without modulator) is assigned a relative receptor activity value of 100. A decrease in activity relative to the control identifies an inhibitor, or antagonist, whereas an increase identifies an enhancer. An increase or decrease in the measured activity of, for example, 10% or more (or any statistically significant difference) can be considered significant in a sample with test agent compared to a sample without test agent; or in a sample with test agent compared to a control sample with test agent but in which the cells do not express TAS2R44 (mock-transfected cells).

To identify antagonists, TAS2R44 activity in the presence of the steviol glycoside agonist with and without a test agent is compared. Antagonists show a reduction of agonist-stimulated receptor activity, for example by at least 10%.

In addition to the functional assays described herein that measure a change in parameters caused by a functional response to agonist binding, changes in agonist binding itself can be determined by binding assays that measure the effects of steviol glycoside binding to TAS2R44. Binding assays are well known in the art and can be tested in solution, in a bilayer membrane, optionally attached to a solid phase, in a lipid monolayer, or in vesicles. Changes in steviol glycoside binding to a TAS2R44 polypeptide can be determined by measuring parameters including but not limited to spectroscopic characteristics (for example fluorescence, absorbance, or refractive index), hydrodynamic methods (employing for example shape), and chromatography, measuring solubility properties of a TAS2R44 polypeptide. In one embodiment, binding assays are biochemical and use membrane extracts from cells/tissue expressing recombinant TAS2R44 polypeptides. A binding assay may, for example, be performed as described for T1Rs by Adler et al. in US20050032158, paragraphs to [0169] to [0198].

Without limitation, various examples of suitable detection methods that measure TAS2R44 receptor activity in assays are now described.

Cells Used in the Assays:

All functional assays may be performed by samples containing cells expressing the receptor on their surfaces or on isolated cell membrane fractions. Useful cells are described herein. Instead of samples with separate cells or cell membranes, tissues from transgenic animals may be used.

Isolated cells or isolated tissues naturally expressing TAS2R44 can be used in the methods described herein. Alternatively TAS2R44 can be expressed using stable or transient expression systems. The generation of a stable cell line is well known, an example is described in example 2 herein. Alternatively, cells transiently expressing TAS2R44 can be used, for example, HEK293T/Gα16-gustducin 44 cells transiently expressing TAS2R44.

Suitable eucaryotic cells include, for example, without limitation, mammalian cells, yeast cells, or insect cells (including Sf9), amphibian cells (including melanophore cells), or worm cells including cells of *Caenorhabditis* (including *Caenorhabditis elegans*). Suitable mammalian cells include, for example, without limitation, COS cells (including Cos-1 and Cos-7), CHO cells, HEK293 cells, HEK293T cells, HEK293 T-Rex™ cells, or other transfectable eucaryotic cell lines. Suitable bacterial cells include without limitation *E. coli*.

Cells may be transfected with TAS2R44 and a G-protein (which links TAS2R44 to a phospholipase C signal transduction pathway) transiently or stably, as is well known in the art. An excellent heterologous expression system that employs the chimeric G-protein G alpha 16-gustducin 44 (also known as G.sub.alpha.16 gust(ducin)44, G.sub.alpha.16gust(ducin) 44, Gα16gust(ducin)44, Gα16gust(ducin)44, Gα16-gustducin 44, or as used herein-below, "G16gust44") which provides for enhanced coupling to taste GPCRs, is described in detail in WO 2004/055048. Alternatively, other chimeric G-proteins based on Gaq-Gustducin described in WO 2004/055048, or other G-Proteins, for example, G16 or G15, may also be used.

TAS2R44 can be expressed in a cell with a G-protein that links the receptor to a signal transduction pathway, for example, the phospholipase C signal transduction pathway, or signal transduction pathways including, for example, the following: adenylate cyclase, guanylate cyclase, phospholipase C, IP3, GTPase/GTP binding, arachinoid acid, cAMP/cGMP, DAG, protein kinase c (PKC), MAP kinase tyrosine kinase, or ERK kinase.

Alternatively, any suitable reporter gene may be linked to a TAS2R44-activation responsive promoter and used to determine TAS2R44 activity, as described in more detail hereinunder.

Vector Constructs Used in Cells Described Herein-above:

Any suitable expression vector may be used, for example, a plasmid vector with expression cassette. For example, pcDNA3.1Zeo or pcDNA5/FRT (Invitrogen, Carlsbad, Calif., US).

For transient expression, any suitable vector can be used, for example, pcDNA5/FRT provides useful results.

TAS2R44 constructs may include so-called tags that add functionality to the resulting protein, for example to enable easier, more stable or more efficient expression, transport, isolation or detection of the TAS2R44 receptor. Tags include but are not limited to a membrane export tag and a tag used for detection of the TAS2R44 including but not limited to immuno detection.

By "membrane export tag" is meant a nucleotide or peptide signal sequence to form the N-terminal part of a protein and to cause the protein to be exported to the membrane. In transformed cells it ensures that the introduced membrane protein (TAS2R bitter taste receptor) translated from the transfected nucleotide sequence is properly targeted to the membrane. Any of the known membrane export tags can be used, for example, without limitation, a membrane export tag from somatostatin, for example, without limitation, rat somatostatin (RSS, SEQ ID NO:3, to form a peptide of 45 amino acids), a rhodopsin tag/fragment, for example, without limitation, bovine rhodopsin, for example, without limitation, the 39 N-terminal aa of rhodopsin or bovine rhodopsin (see for example in Krautwurst et al. 1998, Cell 95(7):917-26), or the relevant fragment from another membrane protein, for example, without limitation, about 7 to about 100 N-terminal aminoacids of a membrane protein.

The HSV tag can be used for immuno detection, or alternatively, it can be replaced by another immuno detection tag or, if no immuno detection is to be performed, it can be left out. Alternative tags for immuno detection are, for example, FLAG® tag (Sigma) with the aminoacid sequence, HA tag, c-MYC tag, HIS tag, HSV tag, VSV-G tag, V5 tag and others.

The vector constructs for expressing the GPCR and/or the G-protein in such cells may be produced in a manner known per se using Polymerase Chain Reactions. After verification of the sequence, cDNA fragments may be sub-cloned into a suitable vector, for example pcDNA 3.1 mammalian expression vector for mammalian cells, and transiently transfected in a corresponding host cell to enable the correct expression of the gene.

After a post-transfection period, for example 48 hours, cell lysates may be prepared, analysed by a Western-Blot analysis in order to confirm the correct expression of the protein. Once correct protein expression is confirmed, suitable cells, for example mammalian cells including HEK293T cells and HEK T-Rex™, may be transfected to generate cells stably expressing the protein according to techniques well known in the art.

Alternatively, a variety of non-mammalian expression vector/host systems can be used to contain and express sequences encoding the TAS2R44 G-Protein coupled receptor (GPCR). These include, for example, microorganisms including bacteria transformed with recombinant bacteriophage, plasmid, or cosmid DNA expression vectors; yeast transformed with yeast expression vectors; insect cell systems infected with viral expression vectors (for example baculovirus), or with bacterial expression vectors (for example pBR322 plasmids).

Examples of specific vectors that may be used with the systems described herein-above are described in "G-protein coupled receptors (Signal Transduction Series)"; Editors: Tatsuya Haga and Gabriel Berstein, 1st ed., CRC Press—Boca Raton Fla.; September 1999.

In bacterial systems, a number of cloning and expression vectors may be selected depending upon the use intended for polynucleotide sequences encoding the GPCR. For example, routine cloning, subcloning, and propagation of polynucleotide sequences encoding a GPCR can be achieved using a multifunctional *E. coli* vector such as pBLUESCRIPT (Stratagene, La Jolla Calif.) or pSPORT1 plasmid (Life Technologies). Ligation of sequences encoding a GPCR into the vector's multiple cloning site disrupts the lacZ gene, allowing a colorimetric screening procedure for identification of transformed bacteria containing recombinant molecules. In addition, these vectors may be useful for in vitro transcription, dideoxy sequencing, single strand rescue with helper phage, and creation of nested deletions in the cloned sequence. When large quantities of a GPCR are needed, for example, for the production of antibodies, vectors which direct high level expression of a GPCR may be used. For example, vectors containing the strong, inducible SP6 or T7 bacteriophage promoter may be used.

Yeast expression systems may be used for production of a GPCR. A number of vectors containing constitutive or inducible promoters, such as alpha factor, alcohol oxidase, and PGH promoters, may be used in the yeast *Saccharomyces cerevisiae* or *Pichia pastoris*. In addition, such vectors direct either the secretion or intracellular retention of expressed proteins and enable integration of foreign sequences into the host genome for stable propagation.

For the expression of heterologous proteins in insect cell lines is, for example, derivatives of the Lepidopteran baculovirus, *Autographa californica* multicapsid nucleo-virus (AcMNPV) can be used. In this system, foreign gene expression is directed by a very strong late viral promoter, either the polyhedrin or p10 promoters, and a wide array of vectors is available that optimises expression and recovery of recombinant proteins. These vectors enable expression of both membrane-bound and secreted proteins at high levels, and also many post-translational modifications known to occur in mammalian systems, including N- and O-linked glycosylation, phosphorylation, acylation, proteolysis and secreted vaccine components. A number of vectors are commercially available, for example the InsectSelect™ System from Invitrogen.

Expression Systems:

In order to express cDNAs encoding the desired proteins (GPCR (TAS2R44) and G-protein), the appropriate cDNA is typically subcloned into an expression vector that contains a strong promoter to direct transcription, a transcription/translation terminator, and a ribosome-binding site for translational initiation. Suitable bacterial promoters are well known in the art, for example, *E. coli, Bacillus* sp., and *Salmonella*, and kits for such expression systems are commercially available. Similarly, eukaryotic expression systems for mammalian cells, yeast, and insect cells are commercially available. The eukaryotic expression vector may be, for example, an adenoviral vector, an adeno-associated vector, or a retroviral vector.

In addition to the promoter, the expression vector typically contains a transcription unit or expression cassette that contains all the additional elements required for the expression of the protein-encoding nucleic acid in host cells. A typical expression cassette thus contains a promoter operably linked to the nucleic acid sequence encoding the protein and signals required for efficient polyadenylation of the transcript, ribosome binding sites, and translation termination. The nucleic acid sequence encoding the protein may typically be linked to a membrane-targeting signal such as the N-terminal 45 amino acids of the rat Somatostatin-3 receptor sequence to promote efficient cell-surface expression of the recombinant protein, which is useful for cell-surface receptors. Additional elements may include, for example, enhancers.

An expression cassette should also contain a transcription termination region downstream of the structural gene to provide for efficient termination. The termination region may be obtained from the same gene as the promoter sequence or may be obtained from different genes.

For expression of the proteins, conventional vectors for expression in eucaryotic or procaryotic cells well known in the art may be used. Examples of vectors include bacterial expression vectors, for example, plasmids including pBR322-based plasmids, pSKF, and pET23D, and fusion expression systems, for example, GST and LacZ.

Expression vectors containing regulatory elements from eukaryotic viruses are typically used in eukaryotic expression vectors, for example SV40 vectors, cytomegalovirus vectors, papilloma virus vectors, and vectors derived from Epstein-Barr virus. Other exemplary eukaryotic vectors include pMSG, pAV009/A$^+$, pMTO10/A$^+$, pMAMneo-5, baculovirus pDSVE, pcDNA3.1, pIRES and any other vector allowing expression of proteins under the direction of the SV40 early promoter, SV40 later promoter, metallothionein promoter, murine mammary tumor virus promoter, Rous sarcoma virus promoter, polyhedrin promoter, or other promoters shown effective for expression in eukaryotic cells.

Some expression systems have markers that provide gene amplification such as thymidine kinase, hygromycin B phosphotransferase, dihydrofolate reductase and the like.

The elements that are typically included in expression vectors may also include a replicon that functions in *E. coli*, a gene encoding drug resistance to permit selection of bacteria that harbor recombinant plasmids, and unique restriction sites in non-essential regions of the plasmid to allow insertion of eukaryotic sequences. The particular drug resistance gene chosen is not critical, any of the many drug resistance genes known in the art are suitable. The prokaryotic sequences are optionally chosen such that they do not interfere with the replication of the DNA in eukaryotic cells, if necessary.

In bacterial systems the GPCR cDNA fragment may be expressed alone or as a fusion protein wherein the GPCR of interest is fused to the *E. coli* periplasmic maltose-binding protein (MBP) wherein the MBP, including its signal peptide, is linked to the amino terminus of the GPCR. The wild-type GPCR cDNA or the MBP:GPCR fusion cDNA is subcloned into a suitable plasmid, for example pBR322, where in *E. coli*, GPCR expression is driven by the lac wild-type promoter. Methods of expression of GPCRs in *E. coli* are described, for example, in "G-protein coupled receptors (Signal Transduction Series)"; Editors: Tatsuya Haga and Gabriel Berstein, 1st ed., pp. 265-280 CRC Press—Boca Raton Fla.; September 1999.

Genetically-engineered yeast systems and insect cell systems which lack endogenous GPCRs provide the advantage of a null background for TAS2R44 screening.

Genetically engineered yeast systems substitute a human GPCR and Gα protein for the corresponding components of the endogenous yeast pheromone receptor pathway. Downstream signaling pathways are also modified so that the normal yeast response to the signal is converted to positive growth on selective media or to reporter gene expression (described by Broach, J. R. and J. Thorner (1996) Nature 384 (supp.):14-16).

Genetically engineered insect systems incorporate a human GPCR and Gα protein that enables receptor coupling the phospholipase C signaling pathway (see for example Knight and Grigliatti, (2004) J Receptors and Signal Transduction 24: 241-256).

Amphibian cell systems, in particular melanophore cells, are described, for example, in WO 92/01810 that describes a GPCR expression system.

Overexpression of TAS2R44:

TAS2R44 may be overexpressed by placing it under the control of a strong constitutive promoter, for example the CMV early promoter. Alternatively, certain mutations of conserved GPCR amino acids or amino acid domains can be introduced to render the employed TAS2R44 GPCR constitutively active.

Transfection of TAS2R44 Expression Vector Constructs into Cells:

Standard transfection methods can be used to produce bacterial, mammalian, yeast or insect cell lines that express large quantities of the protein.

Any known method for introducing nucleotide sequences into host cells may be used. It is only necessary that the particular genetic engineering procedure used be capable of successfully introducing the relevant genes into the host cell capable of expressing the proteins of interest. These methods may involve introducing cloned genomic DNA, cDNA, synthetic DNA or other foreign genetic material into a host cell and include the use of calcium phosphate transfection, polybrene, protoplast fusion, electroporation, liposomes, microinjection, plasma vectors, viral vectors and the like.

For example, without limitation, the T-Rex™ expression system (Invitrogen Corp., Carlsbad, Calif.) may be used. The T-Rex™ System is a tetracycline-regulated mammalian expression system that uses regulatory elements from the *E. coli* Tn10-encoded tetracycline (Tet) resistance operon. Tetracycline regulation in the T-Rex™ System is based on the binding of tetracycline to the Tet repressor and depression of the promoter controlling expression of the gene of interest.

Cell Culture:

After transfection, the transfected cells may be cultured using standard culturing conditions well known in the art. It will be apparent to the skilled person that different cells require different culture conditions including appropriate temperature and cell culture media.

TAS2R44 Receptor Protein Recovery:

If desired, the protein may be recovered from the cell culture using standard techniques. For example, the cells may be burst open either mechanically or by osmotic shock before being subject to precipitation and chromatography steps, the nature and sequence of which will depend on the particular recombinant material to be recovered. Alternatively, the recombinant protein may be recovered from the culture medium in which the recombinant cells had been cultured.

Modulators that May be Identified by the Assays:

Modulators (for example, inhibitors, enhancers, and antagonists, but not agonists) of TAS2R44 receptor activity can be identified as described hereinunder. The type of a modulator may include more than one type at a time, and may depend on the concentration. For example, an agent may act as an agonist in a certain concentration range, but act as a modulator or enhancer of another agonist in another concentration range. Therefore, agents should be tested at different concentrations to identify them as modulators.

There now follows a definition of the agents to be identified in the methods described herein.

A modulator as used herein is an agent that effects an increase or decrease of one or more of the following: the cell surface expression of a receptor, the binding of an agonist (a steviol glycoside) to a receptor, the intracellular response initiated by an active form of the receptor (in the presence of a steviol glycoside), or another physiological response. The modulator modulates (increases or decreases) the response of TAS2R44 to a steviol glycoside.

Modulators include various types of compounds, including small molecules, peptides, proteins, nucleic acids, antibodies or fragments thereof. These can be derived from various sources including synthetic or natural, extracts of natural material, for example from animal, mammalian, insect, plant, bacterial or fungal cell material or cultured cells, or conditioned medium of such cells.

Steviol glycosides as herein described are activators of TAS2R44 which activate TAS2R44 and cause or increase an intracellular response when the activating ligand binds to TAS2R44 compared to the intracellular response in the absence of TAS2R44. Additionally or alternatively, a steviol glycoside may decrease internalization of a cell surface receptor such that the cell surface expression of a receptor is increased as compared to the number of cell surface receptors present on the surface of a cell in the absence of an agonist.

An antagonist is a modulator which binds to the receptor at the same (competitive antagonist) or at a different site (allosteric antagonist) as the agonist/steviol glycoside, but does not activate an intracellular response initiated by an active form of a receptor, thereby inhibiting the intracellular response induced by an agonist as compared to the intracellular response in the presence of an agonist and in the absence of an antagonist.

An inhibitor decreases the binding of an agonist/steviol glycoside to the receptor as compared to the binding of the agonist in the absence of inhibitor, and/or decreases the intracellular response induced by an agonist.

An enhancer increases the binding of an agonist/steviol glycoside to the receptor as compared to the binding of the agonist in the absence of enhancer, and/or increases the intracellular response induced by an agonist.

The activity, or changes in activity, of a receptor binding an agonist and transmitting the signal through, for example, a G-protein (i.e. due to different interactions with modulators) can be determined by the assays described herein-below.

Example Assays to Identify Modulators of the TAS2R44 Receptor:

Detection of Changes of Cytoplasmic Ions or Membrane Voltage:

Cells are loaded with ion-sensitive dyes to report receptor activity, as described in detail in "G-protein coupled receptors (Signal Transduction Series)", CRC Press 1999; 1st Edition; Eds Haga and Berstein. Changes in the concentration of ions in the cytoplasm or membrane voltage are measured using an ion sensitive or membrane voltage fluorescent indicator, respectively.

Calcium Flux:

Intracellular calcium release induced by the activation of GPCRs is detected using cell-permeant dyes that bind to calcium. The calcium-bound dyes generate a fluorescence signal that is proportional to the rise in intracellular calcium. The methods allows for rapid and quantitative measurement of receptor activity.

Cells used are transfected cells that co-express the TAS2R44 GPCR and a G-protein which allows for coupling to the phospholipase C pathway as described herein-above. Negative controls include cells or their membranes not expressing TAS2R44 (mock transfected), to exclude possible non-specific effects of the candidate compound.

The calcium flux detection protocol is described in detail in "G-protein coupled receptors (Signal Transduction Series)"; Editors: Tatsuya Haga and Gabriel Berstein, 1st ed., 424 pp. CRC Press—Boca Raton Fla.; September 1999, and an adapted version with is summarised below:

Day 0: 96-well plates are seeded with 8.5K cells per well and maintained at 37° C. overnight in nutritive growth media.

Day 1: Cells are transfected using 150 ng of TAS2R44 GPCR DNA and 0.3 µl of Lipofectamine 2000 (Invitrogen) per well. Transfected cells are maintained at 37° C. overnight in nutritive growth media.

Day 2: Growth media is discarded and cells are incubated for 1 hour (at room temperature in the dark) with 50 µl of calcium assay solution consisting of 1.5 µM Fluo-4 AM (Molecular Probes) and 2.5 µM probenicid dissolved in C1 buffer solution which contains 130 mM NaCl, 5 mM KCl, 10 mM Hepes, 2 mM CaCl2 and 10 mM glucose (pH 7.4) at 37° C. 125 µl of C1 buffer is added to each well and the plate is further incubated for 30 minutes at room temperature in the dark. Buffer solutions are discarded and plate is washed 5 times with 100 µl C1 buffer as a washing buffer and cells are reconstituted in 200 µl of C1 buffer.

Then the plate is placed in a fluorescent microplate reader, for example, the Flexstation (Molecular Devices) or the FLIPR (Molecular Devices) and receptor activation is initiated following addition of 20 µl of a 10× concentrated agonist stock solution. Fluorescence is continuously monitored for 15 seconds prior to agonist addition and for 45-110 seconds after agonist addition. Receptor activation levels are defined as by the two following equations: % Activation=(Maximum fluorescence−baseline fluorescence/baseline fluorescence) *100 or Fluorescence Increase=Maximum Fluorescence−baseline fluorescence, where baseline fluorescence represents the average fluorescence levels prior to agonist addition.

Useful cells are, without limitation, mammalian cells as described herein-above, for example HEK293T cells and HEK293 T-Rex™ cells. Cells may be transfected with a GPCR and a G-Protein transiently or stably as is well known in the art. An excellent heterologous expression system is described in detail in WO 2004/055048.

A calcium flux assay can be performed, for example, as described in example 1 herein-below.

The identification of a modulator is performed as described above subject to the following modifications. The signals are compared to the baseline level of TAS2R44 activity obtained from recombinant cells expressing TAS2R44 in the presence of an agonist but in the absence of a test agent. An increase or decrease in TAS2R44 activity, for example of at least 2 fold, at least 5 fold, at least 10 fold, at least a 100 fold, or more identifies a modulator.

Alternatively, the identification involves an increase or decrease fluorescence intensity of, for example, 10% or more, when compared to a sample without modulator, or when compared to a sample with modulator but in cells that do not express the TAS2R44 polypeptide (mock-transfected cells):

Adenylate Cyclase Activity:

Assays for adenylate cyclase activity are performed, for example, as described in detail by Kenimer & Nirenberg, 1981, Mol. Pharmacol. 20: 585-591. Reaction mixtures are incubated usually at 37° C. for less than 10 minutes. Following incubation, reaction mixtures are deproteinized by the addition of 0.9 ml of cold 6% trichloroacetic acid. Tubes are centrifuged and each supernatant solution is added to a Dowex AG50W-X4 column. The cAMP fraction from the column is eluted with 4 ml of 0.1 mM imidazole-HCl (pH 7.5) into a counting vial in order to measure the levels of cAMP generated following receptor activation by the agonist. Control reactions should also be performed using protein homogenate from cells that do not express a TAS2R44 polypeptide.

IP3/$Ca^{2+}$ Signals:

In cells expressing G-proteins, signals corresponding to inositol triphosphate (IP3)/$Ca^{2+}$ and thereby receptor activity can be detected using fluorescence. Cells expressing a TAS2R44 GPCR may exhibit increased cytoplasmic calcium levels as a result of contribution from both intracellular stores and via activation of ion channels, in which case it may be desirable, although not necessary, to conduct such assays in calcium-free buffer, optionally supplemented with a chelating agent such as EDTA, to distinguish fluorescence response resulting from calcium release from internal stores.

Phospholipase C/intracellular $Ca^{2+}$ Signals:

TAS2R44 is expressed in a cell with a G-protein that links the receptor to a phospholipase C signal transduction pathway. Changes in intracellular $Ca^{2+}$ concentration are measured, for example using fluorescent $Ca^{2+}$ indicator dyes and/or fluorometric imaging.

GTPase/GTP Binding:

For a GPCR including TAS2R44, a measure of receptor activity is the binding of GTP by cell membranes containing the GPCR. Measured is the G-protein coupling to membranes by detecting the binding of labelled GTP.

Membranes isolated from cells expressing the receptor are incubated in a buffer containing 35S-GTPγS and unlabelled GDP. Active GTPase releases the label as inorganic phosphate, which is detected by separation of free inorganic phosphate in a 5% suspension of activated charcoal in 20 mM $H_3PO_4$, followed by scintillation counting. The mixture is incubated and unbound labelled GTP is removed by filtration onto GF/B filters. Bound and labelled GTP is measured by liquid scintillation counting. Controls include assays using membranes isolated from cells not expressing TAS2R44 (mock-transfected), in order to exclude possible non-specific effects of the test agent. The method is described in detail by Traynor and Nahorski, 1995, Mol. Pharmacol. 47: 848-854.

To identify modulators, as described hereinabove, a change (increase or decrease) of 10% or more in GTP binding or GTPase activity is usually sufficient. However, to identify agonists, the assays described herein-above are performed subject to the following modifications. An agent is identified as an agonist usually if the activity is at least 50% of that of a known agonist (for example perillartine) when the compound is present at 100 mM or less, for example 10 to 500 μM, for example about 100 μM, or if it will induce a level the same as or higher than that induced by a known agonist.

Microphysiometer or Biosensor:

Such assays can be performed as described in detail in Hafner, 2000, Biosens. Bioelectron. 15: 149-158.

Arachinoid Acid:

The intracellular level of arachinoid acid is employed as an indicator of receptor activity. Such a method is described in detail by Gijon et al., 2000, J. Biol. Chem., 275:20146-20156.

cAMP/cGMP:

Intracellular or extracellular cAMP is measured using a cAMP radioimmunoassay (RIA) or cAMP binding protein, for example as described by Horton & Baxendale, 1995, Methods Mol. Biol. 41: 91-105. Alternatively, a number of kits for the measurement of cAMP are commercially available, for example the High Efficiency Fluorescence Polarization-based homogeneous assay by LJL Biosystems and NEN Life Science Products. Alternatively, the intracellular or extracellular levels of cGMP may measured using an immunoassay. For example, the method described in Felley-Bosco et al., Am. J. Resp. Cell and Mol. Biol., 11:159-164 (1994), may be used to determine the level of cGMP. Alternatively an assay kit for measuring cAMP and/or cGMP as described in U.S. Pat. No. 4,115,538 can be used.

Negative controls with mock-transfected cells or extracts thereof to exclude possible non-specific effects of test agents may be used.

DAG/IP3:

Second messengers Diacylglycerol (DAG) and/or inositol triphosphate (IP3), which are released by Phospholipid breakdown, that is caused by receptor activity, can be detected and used as an indicator of GPCR (TAS2R44) activity, for example as described in Phospholipid Signalling Protocols, edited by Ian M. Bird, Totowa, N.J., Humana Press, 1998. Alternatively, kits for the measurement of inositol triphosphates are available commercially from Perkin Elmer and CisBio International.

Negative controls with mock-transfected cells or extracts thereof to exclude possible non-specific effects of test agents may be used.

PKC Activity:

Growth factor receptor tyrosine kinases can signal via a pathway involving activation of Protein Kinase C (PKC), which is a family of phospholipid- and calcium-activated protein kinases.

Increases in gene products induced by PKC show PKC activation and thereby receptor activity. These gene products include, for example, proto-oncogene transcription factor-encoding genes (including c-fos, c-myc and c-jun), proteases, protease inhibitors (including collagenase type I and plasminogen activator inhibitor), and adhesion molecules (including intracellular adhesion molecule I (ICAM I)).

PKC activity may be directly measured as described by Kikkawa et al., 1982, J. Biol. Chem. 257: 13341, where the phosphorylation of a PKC substrate peptide, which is subsequently separated by binding to phosphocellulose paper, is measured. It can be used to measure activity of purified kinase, or in crude cellular extracts. Protein kinase C sample can be diluted in 20 mM HEPES/2 mM DTT immediately prior to the assay.

An alternative assay can be performed using the Protein Kinase C Assay Kit commercially available by PanVera.

The above-described PKC assays are performed on extracts from cells expressing the GPCR (TAS2R44).

Alternatively, activity can be measured through the use of reporter gene constructs driven by the control sequences of genes activated by PKC activation.

Negative controls with mock-transfected cells or extracts thereof to exclude possible non-specific effects of test agents may be used.

MAP Kinase Activity:

MAP kinase activity can be measured using commercially available kits, for example, the p38 MAP Kinase assay kit by New England Biolabs, or the FlashPlate™ MAP Kinase assays by Perkin-Elmer Life Sciences. p42/44 MAP kinases or ERK1/2 can be measured to show GPCR (TAS2R44) activity when cells with Gq and Gi coupled GPCRs are used, and an ERK1/2 assay kit is commercially available by TGR Biosciences, which measures the phosphorylation of endogenous ERK1/2 kinases following GPCR activation.

Alternatively, direct measurements of tyrosine kinase activity through known synthetic or natural tyrosine kinase substrates and labelled phosphate are well known; the activity of other types of kinases (for example, Serine/Threonine kinases) can be measured similarly.

All kinase assays can be performed with both purified kinases and crude extracts prepared from cells expressing one or more TAS2R44 polypeptide.

The substrates of kinases that are used can be either full-length protein or synthetic peptides representing the substrate. Pinna & Ruzzene (1996, Biochem. Biophys. Acta 1314: 191-225) lists a number of phosphorylation substrate sites useful for detecting kinase activities. A number of kinase substrate peptides are commercially available. One that is particularly useful is the "Src-related peptide," RRLIEDAEYAARG (commercially available from Sigma), which is a substrate for many receptor and nonreceptor tyrosine kinases. Some methods require the binding of peptide substrates to filters, then the peptide substrates should have a net positive charge to facilitate binding. Generally, peptide substrates should have at least 2 basic residues and a free-amino terminus. Reactions generally use a peptide concentration of 0.7-1.5 mM.

Negative controls with mock-transfected cells or extracts thereof to exclude possible non-specific effects of test agents may be used.

Transcriptional Reporters/TAS2R44—Responsive Promoter/Reporter Gene:

To identify modulators with reporter gene assays, an at least 2-fold increase or 10% decrease in the signal is significant. An agonist stimulates for example at least 2-fold, 5-fold, 10-fold or more when comparing activity in presence and absence of the test agent.

The intracellular signal initiated by binding of an agonist to TAS2R44 sets in motion a cascade of intracellular events, the ultimate consequence of which is a rapid and detectable change in the transcription or translation of one or more genes.

The activity of the receptor can therefore be determined by measuring the expression of a reporter gene driven by a promoter responsive to TAS2R44 activation.

A "promoter" as used herein is one or more transcriptional control elements or sequences necessary for receptor-mediated regulation of gene expression, including one or more of basal promoter, enhancers and transcription-factor binding sites necessary for receptor-regulated expression. Promoters responsive to the intracellular signals resulting from agonist binding to TAS2R44 are selected and operatively linked to a corresponding promoter-controlled reporter gene whose transcription, translation or ultimate activity is readily detectable and measurable.

Reporter genes may be selected, for example, from luciferase, CAT, GFP, β-lactamase, β-galactosidase, and the so-called "immediate early" genes, c-fos proto-oncogene, transcription factor CREB, vasoactive intestinal peptide (VIP) gene, the somatostatin gene, the proenkephalin gene, the phosphoenolpyruvate carboxy-kinase (PEPCK) gene, genes responsive to NF-κB, and AP-1-responsive genes (including the genes for Fos and Jun, Fos-related antigens (Fra) 1 and 2, IκBα, ornithine decarboxylase, and annexins I and II).

Promoters will be selected according to the selected reporter gene, as will be apparent to the skilled person.

Luciferase, CAT, GFP, β-lactamase, β-galactosidase and assays for the detection of their products are well known in the art. Examples of further reporter genes are described herein-below.

The "immediate early" genes are suitable and are rapidly induced (for example within minutes of contact between the receptor and the effector protein or agonist). Desirable properties in reporter genes include one or more of the following: rapid responsiveness to agonist binding, low or undetectable expression in quiescent cells; induction that is transient and independent of new protein synthesis; subsequent shut-off of transcription requires new protein synthesis; and mRNAs transcribed from these genes which have a short half-life of several minutes to a few hours. Similarly, the promoter may have one, several or all of these properties.

The c-fos proto-oncogene is an example of a gene that is responsive to a number of different stimuli and has an rapid induction. The c-fos regulatory elements include a TATA box that is required for transcription initiation; two upstream elements for basal transcription, and an enhancer, which includes an element with dyad symmetry and which is required for induction by TPA, serum, EGF, and PMA. The 20 bp c-fos transcriptional enhancer element located between −317 and -298 bp upstream from the c-fos mRNA cap site, is essential for serum induction in serum starved NIH 3T3 cells. One of the two upstream elements is located at −63 to −57 and it resembles the consensus sequence for cAMP regulation.

The transcription factor CREB (cyclic AMP responsive element binding protein) is responsive to levels of intracellular cAMP. Therefore, the activation of a receptor that signals via modulation of cAMP levels can be determined by detecting either the binding of the transcription factor, or the expression of a reporter gene linked to a CREB-binding element (termed the CRE, or cAMP response element). The DNA sequence of the CRE is TGACGTCA. Reporter constructs responsive to CREB binding activity are described in U.S. Pat. No. 5,919,649.

Other suitable reporter genes and their promoters include the vasoactive intestinal peptide (VIP) gene and its promoter which is cAMP responsive; the somatostatin gene and its promoter which is cAMP responsive; the proenkephalin and its promoter which is responsive to cAMP, nicotinic agonists, and phorbol esters; and the phosphoenolpyruvate carboxy-kinase (PEPCK) gene and its promoter which is cAMP responsive.

Additional examples of reporter genes and their promoters that are responsive to changes in GPCR activity include the AP-1 transcription factor and NF-κB.

The AP-1 promoter is characterised by a consensus AP-1 binding site which is the palindrome TGA(C/G)TCA. The AP-1 site is also responsible for mediating induction by tumor promoters including the phorbol ester 12-O-tetradecanoylphorbol-β-acetate (TPA), and are therefore sometimes also referred to as a TRE, for TPA-response element. AP-1 activates numerous genes that are involved in the early response of cells to growth stimuli. Examples of AP-1-responsive genes include the genes for Fos and Jun (which proteins themselves make up AP-1 activity), Fos-related antigens (Fra) 1 and 2, IκBα, ornithine decarboxylase, and annexins I and II.

The NF-κB promoter/binding element has the consensus sequence. A large number of genes have been identified as NF-κB responsive, and their control elements can be linked to a reporter gene to monitor GPCR activity. Genes responsive to NF-κB include for example those encoding IL-1β, TNF-α, CCR5, P-selection, Fas ligand, GM-CSF and IκBα. Vectors encoding NF-78 B-responsive reporters are known in the art or can be readily formed using ordinary skill in the art, for example, synthetic NF-κB elements and a minimal promoter, or using the NF-κB-responsive sequences of a gene known to be subject to NF-κB regulation. Further, NF-κB responsive reporter constructs are commercially available from, for example, CLONTECH.

A given promoter construct can easily be tested by exposing GPCR (TAS2R44)-expressing cells, transfected with the construct, to an agonist (for example perillartine). An increase of at least 2-fold in the expression of reporter gene in response to the agonist indicates that the reporter is suitable to measure GPCR (TAS2R44) activity.

Controls for transcription assays include both cells not expressing GPCR (TAS2R44), but carrying the reporter construct, and cells with a promoterless reporter construct.

Agents that modulate GPCR (TAS2R44) activity as shown by reporter gene activation can be verified by using other promoters and/or other receptors to verify GPCR (TAS2R44) specificity of the signal and determine the spectrum of their activity, thereby excluding any non-specific signals, for example non-specific signals via the reporter gene pathway.
Inositol Phosphates (IP) Measurement:

Phosphatidyl inositol (PI) hydrolysis may be determined as described in U.S. Pat. No. 5,436,128, which involves labelling of cells with 3H-myoinositol for at least 48 hours or more. The labelled cells are contacted with a test agent for one hour, then these cells are lysed and extracted in chloroform-methanol-water. This is followed by separating the inositol phosphates by ion exchange chromatography and quantifying them by scintillation counting. For agonists, fold stimulation is determined by calculating the ratio of counts per minute (cpm) in the presence of tested agent, to cpm in the presence of buffer control. Likewise, for inhibitors and antagonists, fold inhibition is determined by calculating the ratio of cpm in the presence of test agent, to cpm in the presence of buffer control (which may or may not contain an agonist).
Binding Assays:

Alternatively to the functional assays described hereinabove that measure a change in parameters caused by a functional response to agonist binding, agonist binding may be determined by binding assays that measure the binding of an agonist to a TAS2R44 receptor.

Binding assays are well known in the art and can be tested in solution, in a bilayer membrane, optionally attached to a solid phase, in a lipid monolayer, or in vesicles. Binding of a modulator to a TAS2R44 polypeptide can be determined, for example, by measuring changes in spectroscopic characteristics (for example fluorescence, absorbance, or refractive index), hydrodynamic methods (employing for example shape), chromatography, measuring solubility properties of a TAS2R44 polypeptide. In one embodiment, binding assays are biochemical and use membrane extracts from cells/tissue expressing recombinant TAS2R44 polypeptides. A binding assay may, for example, be performed as described for T1Rs by Adler et al. in US20050032158, paragraphs [0169] to [0198].

A substantially homologous TAS2R44 protein includes, without limitation, such proteins where all or parts of the protein are replaced with the relevant part of an allelic variant or different species, including a TAS2R44 from mouse, rat, hamster, ape, and dog.

Further, substantially homologous TAS2R44 nucleotide or polypeptide sequences may be formed by conservative mutations and/or point mutations and include, without limitation, any conservatively modified variant as detailed below.

With respect to nucleotide/nucleic acid sequences, conservatively modified variants means nucleic acids which encode identical or essentially identical amino acid sequences (conservatively substituted amino acids, i.e. lysine switched to arginine and further examples as explained herein-below).

Because of the degeneracy of the genetic code, a large number of nucleic acids different in sequence but functionally identical encode any given polypeptide/protein. Such nucleic acid variations are "silent variations," which are one species of conservatively modified variations. Each nucleic acid sequence which encodes a polypeptide also describes every possible silent variation of the nucleic acid. Therefore, each codon in a nucleic acid (except AUG, which is ordinarily the only codon for methionine, and TGG, which is ordinarily the only codon for tryptophan) can be modified to yield a functionally identical nucleic acid sequence that will produce an identical polypeptide. Accordingly, each silent variation of a nucleic acid which encodes a polypeptide is implicit in each given nucleic acid sequence.

With respect to amino acid sequences, amino acid substitutions may be introduced using known protocols of recombinant gene technology including PCR, gene cloning, site-directed mutagenesis of cDNA, transfection of host cells, and in-vitro transcription which may be used to introduce such changes to the TAS2R44 sequence. The variants can then be screened for taste-cell-specific GPCR functional activity. Conservative substitution tables providing functionally similar amino acids are well known in the art. For example, one exemplary guideline to select conservative substitutions includes (original residue followed by exemplary substitution): ala/gly or ser; arg/lys; asn/gln or his; asp/glu; cys/ser; gln/asn; gly/asp; gly/ala or pro; his/asn or gln; ile/leu or val; leu/ile or val; lys/arg or gin or glu; met/leu or tyr or ile; phe/met or leu or tyr; ser/thr; thr/ser; trp/tyr; tyr/trp or phe; val/ile or leu.

An alternative exemplary guideline uses the following six groups, each containing amino acids that are conservative substitutions for one another: 1) Alanine (A), Serine (S), Threonine (T); 2) Aspartic acid (D), Glutamic acid (E); 3) Asparagine (N), Glutamine (Q); 4) Arginine (R), Lysine (1); 5) Isoleucine (I), Leucine (L), Methionine (M), Valine (V); and 6) Phenylalanine (F), Tyrosine (Y), Tryptophan (W).

Another alternative guideline is to allow for all charged amino acids as conservative substitutions for each other whether they are positive or negative.

In addition, individual substitutions, deletions or additions that alter, add or delete a single amino acid or a small percentage (for example up to 26%, or up to 20%, or up to 10%) of amino acids in an encoded sequence are also considered to be conservatively modified variations.

Substantially homologous nucleotide or polypeptide sequences have the degree of sequence identity or hybridize under certain stringent hybridization conditions as indicated below.
% Sequence Identity:

A substantially homologous nucleotide sequence has a % sequence identity of at least at least 90%, at least 95%, or at least 98%.

A substantially homologous polypeptide sequence has a % sequence identity of at least at least 90%, at least 95% or at least 98%.

Alternatively, substantially homologous nucleotide or polypeptide sequences may have a % sequence identity of at least 70%, 80%, or 85%, and are conservative functional variants as detailed herein above.

Calculation of % Sequence Identity is determined as follows. BLAST (Basic Local Alignment Search Tool) is the heuristic search algorithm employed by the programs blastn which is available at the internet website for the National Center for Biotechnology Information.

To determine % identity of a nucleotide query sequence against another nucleotide sequence, Blastn is used, using default parameters of BLAST version 2.2.1.3, including an EXPECT (statistical significance threshold for reporting matches against database sequences) of 10, and DUST filtering.

To determine % identity of a polypeptide query sequence against another polypeptide sequence, Blastp is used, using default parameters of BLAST version 2.2.1.3, including an EXPECT of 10, and DUST filtering.

Stringent Hybridization Conditions:

Nucleotide sequences are considered substantially homologous provided that they are capable of selectively hybridizing to the nucleotide sequences presented herein, or to their complement, under stringent hybrdisation conditions detailed below.

Stringent conditions are temperature of 42° C. in a solution of 50% formamide, 5×SSC, and 1% SDS and washing at 65° C. in a solution of 0.2×SSC and 0.1% SDS (1×SSC=0.15 M NaCl, 0.015 M Na3 Citrate pH 7.0).

Background hybridization may occur because of other nucleotide sequences present, for example, in the cDNA or genomic DNA library being screened.

A signal that is less than 10 fold as intense as the specific interaction observed with the target DNA is considered background. The intensity of interaction may be measured, for example, by radiolabelling the probe, e.g. with 32P.

Kit to Identify a Modulator:

A kit, for example, a screening kit or high throughput screening kit, that comprises recombinant cells that express TAS2R44, or a substantially homologous sequence thereto; and that comprises a steviol glycoside (agonist).

Optionally, the cells further comprise a G-protein for example for calcium signalling. Suitable G-proteins are known and described herein-above; the skilled person is aware how to introduce them to the cells if necessary. A very useful chimeric G-protein is Galpha16-gustducin 44.

The steviol glycoside is provided in suitable concentrations, for example, without limitation, 0.005 to 100 millimolar.

For example, the lower concentration could be at least about 0.005 to about 100 millimolar, for example about 0.01 to 10 millimolar, about 0.05 to 7.5 millimolar, or about 0.3 to 5 millimolar.

For example, the upper end of the concentration range could be up to about 50 to 100 millimolar, about 10 to 50 millimolar, or about 5 to 10 millimolar.

In water, steviols glycosides are insoluble at higher concentrations and depending on the solvent the concentration needs to be sufficiently low to achieve solubility.

Optional kit components may include a suitable medium for culturing the recombinant cells provided, and a solid support to grow the cells on, for example, a cell culture dish or microtiter plate, these optional components will be readily available to the skilled person.

The kit may be used as follows:
(i) Recombinant cells that express the TAS2R44 protein are grown on the solid support;
(ii) test agents at concentrations from about 1 nM to about 100 mM or more are added to the culture medium of defined plates or wells in the presence of the agonist (steviol glycoside) in a suitable concentration; and
(iii) a change in a functional response of the cells is determined by comparing the response in presence and absence of the test agent, and the test agent is thereby identified as a modulator.

For example, (iii) may be performed according to any one of the assays described-herein above, in combination with any one of the detection methods that report receptor activity described herein-above. This may require specifically chosen or adapted recombinant cells, which are also described herein-above.

A suitable assay is, for example, the calcium flux assay to determine activation of TAS2R44 and its change in response to a test agent.

The kit may be used to identify an enhancer as follows:
(i) Recombinant cells that express the TAS2R44 protein are grown on the solid support;
(ii) rest agents at concentrations from about 1 nM to about 100 mM or more are added to the culture medium of defined plates or wells in the presence of a steviol glycoside agonist in a suitable concentration; and
(iii) a change in a functional response of the cells to the agonist is determined by comparing the response in presence and absence of the test agent, and the test agent is thereby identified as an enhancer.

Confirmation of Identified Modulators:

A modulator identified by a method described hereinabove may easily be confirmed by simple sensory experiments using a panel of flavorists or test persons to taste the identified modulators. The compounds are tasted e.g. in water together with a steviol glycoside in comparison to a negative control without modulator to confirm a modulator that enhances the sweet taste of a steviol glycoside or inhibits the bitter taste of a steviol glycoside.

Large Scale Screening Assays:

Transcriptional reporter assays and most cell-based assays described herein-above are well suited for screening libraries for agents that modulate TAS2R44 activity.

The assays may be designed to screen large chemical libraries by automating the assay steps and providing compounds from any convenient source to the assays, which are typically run in parallel (for example in microtiter formats on microtiter plates in robotic assays).

Assays may be run in high throughput screening methods that involve providing a combinatorial chemical or peptide library containing a large number of potential modulators. Such libraries are then screened in one or more assays described herein-above to identify those library agents (particular chemical species or subclasses) that display the activity described herein-above. The modulators thus identified can be directly used or may serve as leads to identify further modulators by making and testing derivatives.

Synthetic compound libraries are commercially available from a number of companies including Maybridge Chemical Co. (Trevillet, Cornwall, UK), Comgenex (Princeton, N.J.), Brandon Associates (Merrimack, N.H.), and Microsource (New Milford, Conn.).

Libraries of Test Agents:

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

A rare chemical library is available from Aldrich (Milwaukee, Wis.).

Libraries of natural compounds in the form of bacterial, fungal, plant and animal extracts are commercially available for example from Pan Laboratories (Bothell, Wash.) or Myco-Search (NC), or are readily produceable by methods well known in the art. Additionally, natural and synthetically produced libraries and compounds are readily modified through conventional chemical, physical, and biochemical means.

Other libraries include protein/expression libraries, cDNA libraries from natural sources, including, for example, foods, plants, animals, bacteria, libraries expressing randomly or systematically mutated variants of one or more polypeptides, genomic libraries in viral vectors that are used to express the mRNA content of one cell or tissue.

In a high throughput assay, it is possible to screen up to several thousand different modulators or agonists in a single day. In particular, each well of a microtiter plate can be used to run a separate assay against a selected potential modulator, or, if concentration or incubation time effects are to be observed, every 5-10 wells can test a single modulator. Thus, a single standard microtiter plate can assay about 100 modulators. If 1536 well plates are used, then a single plate can easily assay from about 100 to about 1500 different compounds. It is possible to assay several different plates per day; assay screens for up to about 6,000-20,000 different compounds is possible.

Types of Test Agents that May be Tested for their TAS2R44 Modulating Effect in the Assay Methods:

The test agents may be any agent including small chemical compounds, chemical polymers, biological polymers, peptides, proteins, sugars, carbohydrates, nucleic acids and lipids. An agent can be a synthetic compound, a mixture of compounds, a natural product or natural sample, for example plant extract, culture supernatant, or tissue sample.

Identified modulators including but not limited to 4-(2,2,3-trimethyl-cyclopentyl)-butanoic acid may be added to food products together with a steviol glycoside to decrease its bitter off-taste and/or enhance its sweet taste.

Consumables include food products, beverages, oral care products, and compositions for admixture to such products, in particular flavour compositions. Flavour compositions may be added to processed foods or beverages during their processing, or they may actually be consumables in their own right, e.g. condiments such as sauces and the like. Sweet tastants are particularly interesting in confectionary and other sweet consumables including desserts, but also in savoury and sweet-sour consumables. Examples of consumables include confectionary products, cakes, cereal products, baker's products, bread products, gums, chewing gums, sauces (condiments), soups, processed foods, cooked fruits and vegetable products, meat and meat products, egg products, milk and dairy products, cheese products, butter and butter substitute products, milk substitute products, soy products, edible oils and fat products, medicaments, beverages, alcoholic drinks, beers, soft drinks, food extracts, plant extracts, meat extracts, condiments, sweeteners, nutraceuticals, pharmaceutical and non-pharmaceutical gums, tablets, lozenges, drops, emulsions, elixirs, syrups and other preparations for making beverages, instant beverages and effervescent tablets.

Sequences of Nucleic Acids and Proteins:

The sequences employed in the constructs and methods described-herein can be found in the sequence listing hereinbelow. They are given in aminoterminal to carboxyterminal direction. All TAS2R sequences are human sequences.

The TAS2R receptor CDS coding sequences are known and have been published under the names and reference numbers indicated below.

SEQ ID NO:1+2 TAS2R44 coding sequence. Human taste receptor type 2 member 44 (TAS2R44, or T2R44), Reference Sequence Accession Number (RefSeq) NM_176885.2, GI:116235453 RefSeq database, The National Center for Biotechnology Information (NCBI)), and the corresponding receptor protein (NP_795366.2 GI:116235454, NCBI RefSeq).

All coding sequences include the ATG start codon but not the stop codon. When cloned into an expression vector, the complete cassette in the vector will include the N-terminal rss tag as a membrane sequence, and the C-terminal HSV tag which provides the STOP codon (as shown as an example in SEQ ID NO:5&6 for the TAS2R44 vector cassette).

SEQ ID NO: 1&2 TAS2R44 coding sequence (nucleic acid+ protein)

SEQ ID NO: 3 RSS Tag includes 45 aminoacids of rat somatostatin and EcoRI site

SEQ ID NO: 4 Includes HSV tag, "T" to get into frame, NotI site and STOP codon

SEQ ID NO: 5&6 hTAS2R44 construct (nucleic acid+protein) (RSS Tag-EcoRI site-TAS2R44-NotI site-HSV Tag with STOP)

There now follows a series of examples that serve to illustrate the above-described methods. The following examples are merely illustrative and should not be construed as limiting the described subject matter including the methods and kit in any manner.

EXAMPLES

All examples use the DNA sequences based on the mRNA for the respective human bitter taste receptor type 2 member (44).

Example 1

Generation of Human TAS2R44 Expression Vector

The full length gene of human TAS2R44 was amplified by polymerase chain reaction (PCR) using gene-specific primers that span the entire coding region.

The TAS2R44 cDNA was subcloned into an expression cassette based on either of the following plasmids/expression vectors: pcDNA3.1Zeo (Invitrogen, Carlsbad, Calif., US). These vectors contain within their multiple cloning sites the nucleotide sequence coding for the first 45 amino acids of the rat somatostatin receptor subtype 3 (included in SEQ ID NO:3, RSS tag) to facilitate cell surface targeting of the transgene, and the nucleotide sequence coding for the herpes simplex virus (HSV) glycoprotein D epitope (HSV epitope) for facilitating immunocytochemical detection, which is included in SEQ ID NO:4, HSV Tag.

RSS tag, TAS2R44, and the HSV tag are fused in frame in the hTASR2 construct of SEQ ID:5 to allow translation into the receptor protein. The resulting receptor cDNA in the expression vector comprises the joined amino acid sequences of TAS2R44 preceded by SEQ ID NO:3 (RSS tag including 45 aminoacids of rat somatostatin) and followed by SEQ ID NO:4 (HSV tag) (in aminoterminal to carboxyterminal direction).

The construct transfected into an expression vector is called pcDNA3.1Zeo-TAS2R44 and allows for expression of the TAS2R44 protein (SEQ ID:6).

Example 2

Example 2a

Generation of Stable Cell Lines

HEK293T/Gα16-gustducin 44 cells were used; they are formed as described in WO 2004/055048. The host cell line HEK-293T is commercially available from the American Tissue Culture Collection (ATCC), ATCC®# CRL-11268

Example 2b

Transient Transfection/Expression of TAS2R44 in HEK293T/Gα16-Gustducin 44 Cells

On day 0, the HEK293T/Gα16-gustducin 44 cells are plated in 96-well black wall, clear-bottom plates at a density of 14,000 cells per well and grown overnight in growth media (DMEM with 10% (v/v) heat-inactivated fetal bovine serum, 2 mM L-glutamine, 100 units/ml penicillin, 100 μg/ml streptomycin).

On day 1, the media is changed to an antibiotic-free and serum-free DMEM.

The cells are transfected with Lipofectamine 2000 (Invitrogen) according to the manufacturers recommendations.

Per well of a 96-well plate, 150 ng of vector DNA (TAS2R44 expression vector of example 1) is diluted in 12.5 μl of DMEM. In a second tube, 0.3 μl of Lipofectamine 2000 is diluted in 12.5 μl of DMEM and incubated for 5 min at room temperature. After the 5 min, both solutions are mixed and incubated for 20 min at RT. The growth medium in the plate is exchanged by 50 μl of DMEM and 25 μl of the lipofectamine/DNA mixture is incubated on the cells for 3-4 hours at 37° in a humidified atmosphere. This mixture is then replaced with an antibiotic-free, serum-containing DMEM.

24 hours post transfection, the cells are used in the Fluo-4 Calcium Assay described in Example 3.

Example 2c

Generation of a Cell Line Stably Expressing G☐16-gustducin44 and TAS2R44

Cell lines that stably expresses TAS2R44 was generated by transfecting pcDNA3.1Zeo-TAS2R44 into HEK293T/Gα16-gustducin 44 cells (both formed as described in example 1). The host cell line HEK-293T is commercially available from the American Tissue Culture Collection (ATCC), ATCC®# CRL-11268.

Transfection was performed as follows:

On day 0, the HEK293T Gα16-gustducin44 cells were seeded in a 6-well plate at a density of 900,000 cells per well and grown over night in selective growth medium.

On day 1, the medium was exchanged with 2 ml of antibiotic-free and serum-free growth medium. 10 μl Lipofectamine 2000 was dissolved in 250 μl DMEM and incubated for 5 minutes at room temperature. In parallel, 4 μg TAS2R44 vector DNA were dissolved in 250 μl DMEM. These two resulting solutions are mixed and incubated for 20 minutes at room temperature before they are added to the cells into the cell culture medium. After 4 hours, the medium is replaced with antibiotic-free, serum-containing growth medium.

The cells were incubated in humidified atmosphere (37° C., 5% $CO_2$).

After 24 hours, the cells were re-plated in selective growth medium (DMEM with 10% (v/v) heat-inactivated fetal bovine serum, 2 mM L-glutamine, 100 units/ml penicillin, 100 μg/ml streptomycin, 200 μg/ml G418 and 200 μg/ml zeocin) and were further incubated in a humidified atmosphere (37° C., 5% $CO_2$).

After 2 to 4 weeks of culture (replacing medium as necessary), zeocin-resistant colonies were selected and expanded.

The expression of TAS2R44 was evaluated by testing for the presence of a functional response to the known TAS2R44 agonist saccharin (as described in WO 2004/029087) in addition to a F(I) steviol glycoside, which was determined via automated calcium imaging on the FLIPR-TETRA™ (Molecular Devices, Sunnyvale, Calif., US) as described in example 3. One clone was selected resulting in the HEK293T/Gα16-gustducin 44/TAS2R44 cell line.

Example 3

Fluo-4 Calcium Assay

Fluo-4AM (Invitrogen, Carlsbad, Calif., US) is a fluorescent indicator of intracellular calcium dynamics (change in concentration) and allows monitoring changes in the calcium concentration, particularly an increase in response to receptor activation occurring after agonist exposure.

At day 0, the HEK293T cell line expressing Gα16-gustducin44 and a TAS2R bitter taste receptor formed as described in examples 2b or 2c was seeded in antibiotic-free growth medium (standard DMEM with 10% (v/v) heat-inactivated fetal bovine serum, 2 mM L-glutamine standard DMEM with 10% (v/v) heat-inactivated fetal bovine serum, 2 mM L-glutamine, 100 units/ml penicillin, and 100 μg/ml streptomycin) into black wall/clear bottom 96-well plates, coated with poly(ethylenimine) (0.005% v/v) at a concentration of 15,000 cells per well and incubated for 48 hours in humidified atmosphere (37° C., 5% $CO_2$).

At the time of the assay, the growth medium was discarded and the cells were in humidified atmosphere (37° C., 5% $CO_2$) for 1 hour with 50 μl of loading buffer consisting of 1.5 μM Fluo-4 AM and 2.5 μM probenicid (Sigma-Aldrich, St. Louis, Mo., US) in DMEM.

Afterwards, the 96-well plate was washed 5 times with 100 μl of assay buffer (130 mM NaCl, 5 mM KCl, 10 mM HEPES, 2 mM $CaCl_2$, and 5 mM dextrose, pH 7.4) per well, using an automated plate washer (BioTek). The plate was further incubated for 30 minutes at room temperature in the dark to allow for complete de-esterification of the Fluo-4. Afterwards the plate was washed 5 times with 100 μl of assay buffer per well, and reconstituted with 100 μl of assay buffer per well.

For assay reading, the plate was placed in a Fluorometric Imaging Plate Reader (FLIPR) (FLIPR-TETRA™, Molecular Devices, Sunnyvale, Calif., US), and receptor activation was initiated by addition of 100 μl of a twofold concentrated agonist stock solution (to give the desired agonist end concentration when added to the 100 microliter assay buffer volume), which was prepared in assay buffer.

Fluorescence was continuously monitored for 20 seconds to give a signal baseline (averaged to give $F_0$) prior to agonist addition and for 120 seconds after agonist addition. The change in signal divided by $F_0$ gives $\Delta F/F_0$ indicated in the table, with $\Delta F$ being the maximum signal occurring within the 120 seconds minus the minimum signal (occurring within the 120 seconds after agonist addition.

All data was collected from at least two independent experiments each carried out in triplicate.

A concentration-response analysis was performed and $EC_{50}$ values were calculated by nonlinear regression using the function $f(x)=(a-d)/(1+(x/C)^{nh})+d$; with a=minimum signal, d=maximum signal, nh=hill coefficient, $C=EC_{50}$, and x=agonist concentration. $EC_{50}$ is the molar concentration of an agonist which produces 50% of the maximum possible effective response for that agonist. A more potent agonist will have a lower $EC_{50}$ value.

The obtained calcium signals were corrected for the response of cells expressing only the G Proteinα subunit (Gα16-gustducin44) and normalized to the fluorescence of cells prior to the stimulus using ΔF/F0 (Fmax−Fmin/F0).

Example 4

Activation of TAS2R44 by Saccharin

To confirm that the cell line formed in example 2c stably expresses the bitter taste receptor TAS2R44, a concentration-response curve for saccharin, a known agonist of TAS2R44, was generated. As a negative control, HEK293T Gα16gustducin44 cells (that do not express TAS2R44) were exposed to saccharin. The results are calculated as described in example 4 and are shown in table 1. The standard deviation (+/−STD) is also indicated.

TABLE 1

Activation of TAS2R44 by different concentrations of saccharin.

| Saccharin [mM] | TAS2R44 $\Delta F/F_0$ | TAS2R44 ± STD | Neg. Control $\Delta F/F_0$ | Neg. Control ± STD |
|---|---|---|---|---|
| 10.0000 | 1.354 | 0.131 | 0.020 | 0.022 |
| 5.0000 | 1.258 | 0.176 | 0.018 | 0.018 |
| 2.5000 | 1.150 | 0.142 | 0.013 | 0.013 |
| 1.2500 | 0.947 | 0.140 | 0.014 | 0.012 |
| 0.6250 | 0.668 | 0.120 | 0.014 | 0.005 |
| 0.3125 | 0.388 | 0.077 | 0.012 | 0.001 |
| 0.1563 | 0.181 | 0.041 | 0.014 | 0.006 |
| 0.0781 | 0.075 | 0.016 | 0.014 | 0.003 |
| 0.0391 | 0.024 | 0.005 | 0.016 | 0.011 |

The negative control did not show any significant change in signal upon exposure to saccharin, and the signal did not increase or decrease together with the saccharin concentration, demonstrating the absence of agonist-induced receptor activation. The $EC_{50}$ was calculated as described in example 3. The calculated $EC_{50}$ value for saccharin and TAS2R44 was 0.65±0.02 mM.

Example 5

Activation of TAS2R44 by Steviol Glycosides

The intracellular calcium response following addition of steviol glycosides (stevioside, rebaudioside A) was determined in HEK293T cell line stably expressing Gα16-gustducin44 and TAS2R44 formed as described in example 2a.

As a negative control to determine unspecific signals, each of the applied concentrations of each F(I) steviol glycoside was applied to cells expressing only Gα16gustducin44. The results are shown in the tables below.

Activation of TAS2R44 by different concentrations of stevioside (ΔF/F0 values +/− STD)

| Stevioside [mM] | TAS2R44 $\Delta F/F_0$ | TAS2R44 ± STD | Neg. Control $\Delta F/F_0$ | Neg. Control ± STD |
|---|---|---|---|---|
| 5.000 | 1.155 | 0.403 | 0.435 | 0.130 |
| 2.500 | 0.677 | 0.186 | 0.010 | 0.050 |
| 0.625 | 0.451 | 0.107 | 0.062 | 0.021 |
| 0.125 | 0.230 | 0.054 | 0.063 | 0.037 |
| 0.063 | 0.136 | 0.031 | 0.065 | 0.024 |
| 0.031 | 0.112 | 0.032 | 0.074 | 0.047 |
| 0.016 | 0.096 | 0.027 | 0.059 | 0.027 |
| 0.008 | 0.079 | 0.023 | 0.059 | 0.020 |
| 0.004 | 0.082 | 0.024 | 0.061 | 0.031 |

Activation of TAS2R44 by different concentrations of rebaudioside A (ΔF/F0 values +/− STD)

| Rebaudioside [mM] | TAS2R44 $\Delta F/F_0$ | TAS2R44 ± STD | Neg. Control $\Delta F/F_0$ | Neg. Control ± STD |
|---|---|---|---|---|
| 5.000 | 0.62625 | 0.074375 | 0.208 | 0.070606 |
| 2.500 | 0.781875 | 0.04665 | 0.153 | 0.036143 |
| 0.625 | 0.7025 | 0.092844 | 0.1115 | 0.031502 |
| 0.125 | 0.32 | 0.041312 | 0.087 | 0.020026 |
| 0.063 | 0.161875 | 0.046507 | 0.0685 | 0.013485 |
| 0.031 | 0.168125 | 0.203346 | 0.063 | 0.010809 |
| 0.016 | 0.0975 | 0.024358 | 0.054 | 0.010463 |
| 0.008 | 0.079375 | 0.02435 | 0.0635 | 0.028335 |
| 0.004 | 0.076875 | 0.017017 | 0.061 | 0.017442 |

A significant increase in calcium signaling was observed upon addition of both F(I) steviol glycosides, stevioside and rebaudioside A, in cells stably expressing human TAS2R44. No significant change was seen in the negative control, which is the host cells expressing only the Gα16-gustducin44. This shows the specificity of the F(I) steviol glycosides as a TAS2R44 agonists.

Furthermore, more than 15 other TAS2R receptors that were tested were found not to be activated by F(I) steviol glycosides.

The calculated $EC_{50}$ value was 2.2 mM for stevioside. The results demonstrate that TAS2R44 is activated by stevioside. A comparison to the EC50 of saccharin (example 4, 0.65±0.02 mM) show that stevioside is a similarly potent agonist as saccharin, which is a known agonist of TAS2R44.

The calculated $EC_{50}$ value was 0.7 mM for rebaudioside A. The results demonstrate that TAS2R44 is activated by rebaudioside A. A comparison to the EC50 of saccharin (example 4, 0.65±0.02 mM) show that rebaudioside A is a similarly potent agonist as saccharin.

Furthermore, cyclamate and aspartame, sweeteners with a known bitter off-note, were also tested and found not to be agonists for TAS2R44, further indicating the highly specific receptor activation by F(I) steviol glycosides.

Example 6

Identification of Antagonists of the Response of TAS2R44 to Steviol Glycosides All cells were HEK293T cells stably expressing Gα16-gustducin44, or expressing Gα16-gustducin44 and TAS2R44.

The method was carried out as described in example 3 subject to the following modifications:

The samples were tested with and without candidate bitter blocker and the signals were compared. The candidate bitter blocker was dissolved in dimethylsulfoxide (DMSO), and a negative control with equivalent DMSO concentration (0.02%) was performed accordingly to exclude a potential inhibitory effect of the solvent. Furthermore, a control with the relevant steviol glycoside and DMSO (0.02%) was performed accordingly (see table in example 5).

All data was calculated as $\Delta F/F_0$ and the standard deviation (STD) is indicated in each table, see results for the identified bitter blocker 4-(2,2,3-trimethyl-cyclopentyl)-butanoic acid below.

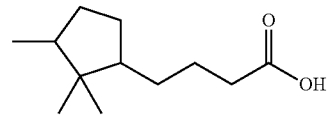

4-(2,2,3-trimethyl-cyclopentyl)-butanoic acid

| bitter blocker [μM] | TAS2R44 $\Delta F/F_0$ | TAS2R44 ± STD |
|---|---|---|
| 100.0 | 0.212 | 0.137 |
| 50.00 | 0.238 | 0.064 |
| 25.00 | 0.252 | 0.081 |
| 12.50 | 0.293 | 0.112 |
| 6.250 | 0.328 | 0.124 |
| 3.125 | 0.430 | 0.196 |
| 1.563 | 0.431 | 0.143 |
| 0.781 | 0.491 | 0.146 |
| 0.391 | 0.555 | 0.137 |
| 0.195 | 0.596 | 0.135 |
| 0.098 | 0.665 | 0.180 |

Response of TAS2R44 expressing cells to 2.2 mM stevioside (EC$_{50}$) alone or in the presence of bitter blocker or negative control The stevioside positive control average was $\Delta F/F0=0.733$, and the IC50 concentration for stevioside was 0.578 μM.

Response of TAS2R44 expressing cells to 0.7 mM rebaudioside A (EC$_{50}$) alone or in the presence of bitter blocker or negative control

| bitter blocker [μM] | TAS2R44 $\Delta F/F_0$ | TAS2R44 ± STD |
|---|---|---|
| 100.0 | 0.22375 | 0.048042 |
| 50.00 | 0.234688 | 0.031926 |
| 25.00 | 0.2275 | 0.034267 |
| 12.50 | 0.205625 | 0.045361 |
| 6.250 | 0.179375 | 0.045433 |
| 3.125 | 0.1225 | 0.033793 |
| 1.563 | 0.132813 | 0.053776 |
| 0.781 | 0.215625 | 0.079146 |
| 0.391 | 0.2825 | 0.078082 |
| 0.195 | 0.367813 | 0.089433 |
| 0.098 | 0.402188 | 0.116667 |

The rebaudioside positive control average was $\Delta F/F0=0.4625$, and the IC50 concentration for rebaudioside was 0.357 μM.

The results for the negative control (agonists applied to cells expressing only Gα16gustducin44 but no TAS2 receptor) demonstrate the specificity of the inhibition of TAS2R44 by the bitter blocker (4-(2,2,3-trimethyl-cyclopentyl)-butanoic acid).

Example 7

Sensory Evaluation of
4-(2,2,3-trimethyl-cyclopentyl)-butanoic acid
Reducing the Bitter Taste of a Steviol Glycoside 4-(2,2,3-trimethyl-cyclopentyl)-butanoic acid was sensorically evaluated for its bitter blocking characteristics by 8 bitter-sensitive panelists.

The following samples in water were evaluated and compared in their bitter taste/aftertaste:
Rebaudioside A (60 ppm) with bitter blocker (10 ppm)
Rebaudioside A (60 ppm) without bitter blocker
Rebaudioside A (230 ppm, isosweet to 7% sugar in water)
Rebaudioside A (230 ppm) with bitter blocker (10 ppm 30 ppm and 50 ppm)

20 ml of each sample was presented in random order.

All panelists found that 4-(2,2,3-trimethyl-cyclopentyl)-butanoic acid blocked or significantly reduced the bitter taste/aftertaste of Rebaudioside A.

10 ppm bitter blocker blocked the upfront bitterness but some lingering bitterness/aftertaste remained.

30 ppm and 50 ppm bitter blocker showed an improved effect to reduce the lingering bitterness/bitter aftertaste.

60 ppm completely blocked the bitterness including the bitter aftertaste in water.

While the methods and kit have been described above have been presented in connection with illustrative embodiments, it is to be understood that other similar embodiments may be used or modifications and additions may be made to the described embodiments for performing the same function without deviating therefrom. Further, all embodiments disclosed are not necessarily in the alternative, as various embodiments of the invention may be combined to provide the desired characteristics. Variations can be made by one having ordinary skill in the art without departing from the scope of the invention. Therefore, the methods and kit should not be limited to any single embodiment, but rather construed in breadth and scope in accordance with the recitation of the attached claims.

The invention claimed is:

1. A method of identifying an agent that modulates the taste of a steviol glycoside comprising the steps of:
   (i) contacting cells that express a bitter taste receptor that is able to be activated by a steviol glycoside in the presence of at least one agent; and
   (ii) determining whether the at least one agent affects binding of said bitter taste receptor to the one or more steviol glycoside, or a functional response to the binding of said bitter taste receptor to the one or more steviol glycoside, wherein the bitter taste receptor comprises a polypeptide having at least 90% sequence identity to SEQ ID NO: 2, with the proviso that the cells are not unmanipulated cells in their natural environment.

2. The method of claim 1, wherein the one or more steviol glycoside is a steviol glycoside of formula F(I),

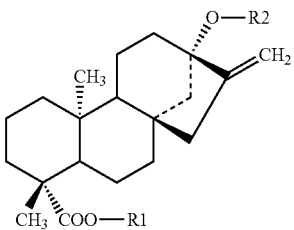

F(I)

wherein R1 and R2 are residues independently selected from the group consisting of H, beta-Glc, beta-Glc-beta-Glc(2->1), beta-Glc[beta-Glc(3->1)]-beta-Glc(2->1), beta-Glc-alpha-Rha(2->1), beta-Glc[beta-Glc(3->1)]-alpha-Rha(2->1), and beta-Glc[beta-Glc(3->1)]-alpha-Xyl(2->1).

3. The method according to claim 1, wherein the bitter taste receptor is encoded by a nucleotide sequence selected from the group consisting of a nucleotide sequence with a sequence identity of at least 90% of SEQ ID NO:1 and, a nucleotide sequence with a sequence identity of at least 90% of SEQ ID NO:1 as determined by hybridisation, under stringent hybridization conditions at a temperature of 42° C. in a solution of 50% formamide, 5×SSC, and 1% SDS, and washing at 65° C. in a solution of 0.2×SSC and 0.1% SDS.

4. The method according to claim 3 wherein the nucleotide sequence comprises SEQ ID NO:4 (HSV tag) at or near its end to form the C-terminus in the corresponding protein.

5. The method according to claim 3 wherein the bitter taste receptor comprises one or more tags.

6. The method according to claim 5 wherein the tag is a membrane export tag.

7. The method according to claim 5 wherein the tag is a detection tag.

8. The method according to claim 1, wherein the bitter taste receptor comprises a conservative functional variant of SEQ ID NO: 2 that is able to be activated by one or more steviol glycoside.

9. The method according to claim 1, wherein the cells also express a G-Protein.

10. The method of claim 9 wherein the G-Protein is selected from the group consisting of Gaq-Gustducin, G alpha 16-gustducin 44, and a chimeric G-Protein.

11. The method according to claim 1, wherein step (ii) comprises measuring a change in or caused by intracellular messengers.

12. The method according to claim 1, comprising determining the functional response by measuring a change in an intracellular messenger selected from IP3 and calcium$^{2+}$.

13. The method according to claim 1, wherein said cells are selected from the group consisting of eucaryotic cells, yeast cells, insect cells, mammalian cells, amphibian cells, worm cells and combinations thereof.

14. The method according to claim 13, wherein the cells comprise mammalian cells.

15. The method according to claim 14 wherein the cell comprise mammalian cells selected from the group consisting of CHO, COS, HeLa, HEK-293 cells and combinations thereof.

16. The method according to claim 1, wherein step (i) further comprises contacting the bitter taste receptor with a test agent in presence of calcium.

17. The method of claim 1 wherein the bitter taste receptor comprises a polypeptide sequence with a sequence identity of at least 95% to SEQ ID NO:2.

18. The method of claim 1 wherein the bitter taste receptor comprises a polypeptide sequence with a sequence identity of at least 98% to SEQ ID NO:2.

19. A kit comprising:
 (i) recombinant cells that express a bitter taste receptor, and
 (ii) one or more steviol glycoside,
for combined use to identify test agents as modulators of the taste of a steviol glycoside,
wherein the bitter taste receptor comprises a polypeptide having at least 90% sequence identity to SEQ ID NO: 2.

20. A method of using the kit of claim 19, comprising the steps of:
 (i) growing recombinant cells that express the bitter taste receptor,
 (ii) adding at least one test agent in the presence of one or more steviol glycoside, and
 (iii) determining a change in a functional response of the cells by comparing the response in presence and absence of the test agent,
to identify test agents that modulate the taste of sucralose.

21. The method of claim 19 wherein the bitter taste receptor comprises a polypeptide sequence with a sequence identity of at least 95% to SEQ ID NO:2.

22. The method of claim 19 wherein the bitter taste receptor comprises a polypeptide sequence with a sequence identity of at least 98% to SEQ ID NO:2.

23. A method of identifying an agent that modulates a bitter taste receptor, the method comprising the steps of:
 (i) measuring a parameter that changes in response to the steviol glycoside binding to the bitter taste receptor, and
 (ii) determining a change of the parameter in response to a test agent, in comparison to a negative control and thereby identifying a modulator of the taste of the steviol glycoside,
wherein the bitter taste receptor comprises a polypeptide having at least 90% sequence identity to SEQ ID NO: 2.

24. Method according to claim 23 wherein step (i) is performed by a method selected from the group consisting of: fluorescence spectroscopy, NMR spectroscopy, measuring of one or more of absorbance, refractive index, hydrodynamic methods, chromatography, measuring solubility, biochemical methods, wherein the methods measure the properties of the bitter taste receptor in a suitable environment which is selected from the group consisting of solution, bilayer membrane, attached to a solid phase, in a lipid monolayer, bound on a membrane, and in vesicles.

* * * * *

SEQUENCE LISTING

```
<160> NUMBER OF SEQ ID NOS: 6

<210> SEQ ID NO 1
<211> LENGTH: 930
<212> TYPE: DNA
<213> ORGANISM: Homo sapiens
<220> FEATURE:
<221> NAME/KEY: CDS
<222> LOCATION: (1)..(930)

<400> SEQUENCE: 1 atg aca act ttt ata ccc atc att ttt tcc agt gtg gta gtg gtt cta      48
```

|     |     |     |     |     |     |     |     |     |     |     |     |     |     |     |     |     |
|---|---|---|---|---|---|---|---|---|---|---|---|---|---|---|---|---|
| Met | Thr | Thr | Phe | Ile | Pro | Ile | Ile | Phe | Ser | Ser | Val | Val | Val | Leu | | |
| 1 | | | | 5 | | | | | 10 | | | | | 15 | | |
| ttt | gtt | att | gga | aat | ttt | gct | aat | ggc | ttc | ata | gca | ttg | gta | aat | tcc | 96 |
| Phe | Val | Ile | Gly | Asn | Phe | Ala | Asn | Gly | Phe | Ile | Ala | Leu | Val | Asn | Ser | |
| | | | 20 | | | | | 25 | | | | | 30 | | | |
| att | gag | cgg | gtc | aag | aga | caa | aag | atc | tct | ttt | gct | gac | cag | att | ctc | 144 |
| Ile | Glu | Arg | Val | Lys | Arg | Gln | Lys | Ile | Ser | Phe | Ala | Asp | Gln | Ile | Leu | |
| | | 35 | | | | | 40 | | | | | 45 | | | | |
| act | gct | ctg | gcg | gtc | tcc | aga | gtt | ggt | ttg | ctc | tgg | gta | tta | tta | tta | 192 |
| Thr | Ala | Leu | Ala | Val | Ser | Arg | Val | Gly | Leu | Leu | Trp | Val | Leu | Leu | Leu | |
| | 50 | | | | | 55 | | | | | 60 | | | | | |
| aat | tgg | tat | tca | act | gtg | ttt | aat | cca | gct | ttt | tat | agt | gta | gaa | gta | 240 |
| Asn | Trp | Tyr | Ser | Thr | Val | Phe | Asn | Pro | Ala | Phe | Tyr | Ser | Val | Glu | Val | |
| 65 | | | | 70 | | | | | 75 | | | | | 80 | | |
| aga | act | act | gct | tat | aat | gtc | tgg | gca | gta | acc | ggc | cat | ttc | agc | aac | 288 |
| Arg | Thr | Thr | Ala | Tyr | Asn | Val | Trp | Ala | Val | Thr | Gly | His | Phe | Ser | Asn | |
| | | | | 85 | | | | | 90 | | | | | 95 | | |
| tgg | ctt | gct | act | agc | ctc | agc | ata | ttt | tat | ttg | ctc | aag | att | gcc | aat | 336 |
| Trp | Leu | Ala | Thr | Ser | Leu | Ser | Ile | Phe | Tyr | Leu | Leu | Lys | Ile | Ala | Asn | |
| | | | 100 | | | | | 105 | | | | | 110 | | | |
| ttc | tcc | aac | ctt | att | ttt | ctt | cac | tta | aag | agg | aga | gtt | aag | agt | gtc | 384 |
| Phe | Ser | Asn | Leu | Ile | Phe | Leu | His | Leu | Lys | Arg | Arg | Val | Lys | Ser | Val | |
| | | 115 | | | | | 120 | | | | | 125 | | | | |
| att | ctg | gtg | atg | ctg | ttg | ggg | cct | tta | cta | ttt | ttg | gct | tgt | caa | ctt | 432 |
| Ile | Leu | Val | Met | Leu | Leu | Gly | Pro | Leu | Leu | Phe | Leu | Ala | Cys | Gln | Leu | |
| | 130 | | | | | 135 | | | | | 140 | | | | | |
| ttt | gtg | ata | aac | atg | aaa | gag | att | gta | cgg | aca | aaa | gaa | tat | gaa | gga | 480 |
| Phe | Val | Ile | Asn | Met | Lys | Glu | Ile | Val | Arg | Thr | Lys | Glu | Tyr | Glu | Gly | |
| 145 | | | | 150 | | | | | 155 | | | | | 160 | | |
| aac | ttg | act | tgg | aag | atc | aaa | ttg | agg | agt | gca | gtg | tac | ctt | tca | gat | 528 |
| Asn | Leu | Thr | Trp | Lys | Ile | Lys | Leu | Arg | Ser | Ala | Val | Tyr | Leu | Ser | Asp | |
| | | | | 165 | | | | | 170 | | | | | 175 | | |
| gcg | act | gta | acc | acg | cta | gga | aac | tta | gtg | ccc | ttc | act | ctg | acc | ctg | 576 |
| Ala | Thr | Val | Thr | Thr | Leu | Gly | Asn | Leu | Val | Pro | Phe | Thr | Leu | Thr | Leu | |
| | | | 180 | | | | | 185 | | | | | 190 | | | |
| cta | tgt | ttt | ttg | ctg | tta | atc | tgt | tct | ctg | tgt | aaa | cat | ctc | aag | aag | 624 |
| Leu | Cys | Phe | Leu | Leu | Leu | Ile | Cys | Ser | Leu | Cys | Lys | His | Leu | Lys | Lys | |
| | 195 | | | | | 200 | | | | | 205 | | | | | |
| atg | cag | ctc | cat | ggt | aaa | gga | tct | caa | gat | ccc | agc | acc | aag | gtc | cac | 672 |
| Met | Gln | Leu | His | Gly | Lys | Gly | Ser | Gln | Asp | Pro | Ser | Thr | Lys | Val | His | |
| 210 | | | | 215 | | | | | 220 | | | | | | | |
| ata | aaa | gct | ttg | caa | act | gtg | atc | ttt | ttc | ctc | ttg | tta | tgt | gcc | gtt | 720 |
| Ile | Lys | Ala | Leu | Gln | Thr | Val | Ile | Phe | Phe | Leu | Leu | Leu | Cys | Ala | Val | |
| 225 | | | | 230 | | | | | 235 | | | | | 240 | | |
| tac | ttt | ctg | tcc | ata | atg | ata | tca | gtt | tgg | agt | ttt | ggg | agt | ctg | gaa | 768 |
| Tyr | Phe | Leu | Ser | Ile | Met | Ile | Ser | Val | Trp | Ser | Phe | Gly | Ser | Leu | Glu | |
| | | | | 245 | | | | | 250 | | | | | 255 | | |
| aac | aaa | cct | gtc | ttc | atg | ttc | tgc | aaa | gct | att | aga | ttc | agc | tat | cct | 816 |
| Asn | Lys | Pro | Val | Phe | Met | Phe | Cys | Lys | Ala | Ile | Arg | Phe | Ser | Tyr | Pro | |
| | | | 260 | | | | | 265 | | | | | 270 | | | |
| tca | atc | cac | cca | ttc | atc | ctg | att | tgg | gga | aac | aag | aag | cta | aag | cag | 864 |
| Ser | Ile | His | Pro | Phe | Ile | Leu | Ile | Trp | Gly | Asn | Lys | Lys | Leu | Lys | Gln | |
| | | 275 | | | | | 280 | | | | | 285 | | | | |
| act | ttt | ctt | tca | gtt | ttg | cgg | caa | gtg | agg | tac | tgg | gtg | aaa | gga | gag | 912 |
| Thr | Phe | Leu | Ser | Val | Leu | Arg | Gln | Val | Arg | Tyr | Trp | Val | Lys | Gly | Glu | |
| | 290 | | | | | 295 | | | | | 300 | | | | | |
| aag | cct | tca | tct | cca | tag | | | | | | | | | | | 930 |
| Lys | Pro | Ser | Ser | Pro | | | | | | | | | | | | |
| 305 | | | | | | | | | | | | | | | | |

```
<210> SEQ ID NO 2
<211> LENGTH: 309
<212> TYPE: PRT
<213> ORGANISM: Homo sapiens

<400> SEQUENCE: 2

Met Thr Thr Phe Ile Pro Ile Ile Phe Ser Ser Val Val Val Leu
1               5                   10                  15

Phe Val Ile Gly Asn Phe Ala Asn Gly Phe Ile Ala Leu Val Asn Ser
            20                  25                  30

Ile Glu Arg Val Lys Arg Gln Lys Ile Ser Phe Ala Asp Gln Ile Leu
            35                  40                  45

Thr Ala Leu Ala Val Ser Arg Val Gly Leu Leu Trp Val Leu Leu Leu
        50                  55                  60

Asn Trp Tyr Ser Thr Val Phe Asn Pro Ala Phe Tyr Ser Val Glu Val
65                  70                  75                  80

Arg Thr Thr Ala Tyr Asn Val Trp Ala Val Thr Gly His Phe Ser Asn
                    85                  90                  95

Trp Leu Ala Thr Ser Leu Ser Ile Phe Tyr Leu Leu Lys Ile Ala Asn
                100                 105                 110

Phe Ser Asn Leu Ile Phe Leu His Leu Lys Arg Arg Val Lys Ser Val
            115                 120                 125

Ile Leu Val Met Leu Leu Gly Pro Leu Leu Phe Leu Ala Cys Gln Leu
130                 135                 140

Phe Val Ile Asn Met Lys Glu Ile Val Arg Thr Lys Glu Tyr Glu Gly
145                 150                 155                 160

Asn Leu Thr Trp Lys Ile Lys Leu Arg Ser Ala Val Tyr Leu Ser Asp
                    165                 170                 175

Ala Thr Val Thr Thr Leu Gly Asn Leu Val Pro Phe Thr Leu Thr Leu
                180                 185                 190

Leu Cys Phe Leu Leu Leu Ile Cys Ser Leu Cys Lys His Leu Lys Lys
            195                 200                 205

Met Gln Leu His Gly Lys Gly Ser Gln Asp Pro Ser Thr Lys Val His
210                 215                 220

Ile Lys Ala Leu Gln Thr Val Ile Phe Phe Leu Leu Leu Cys Ala Val
225                 230                 235                 240

Tyr Phe Leu Ser Ile Met Ile Ser Val Trp Ser Phe Gly Ser Leu Glu
                    245                 250                 255

Asn Lys Pro Val Phe Met Phe Cys Lys Ala Ile Arg Phe Ser Tyr Pro
                260                 265                 270

Ser Ile His Pro Phe Ile Leu Ile Trp Gly Asn Lys Lys Leu Lys Gln
            275                 280                 285

Thr Phe Leu Ser Val Leu Arg Gln Val Arg Tyr Trp Val Lys Gly Glu
        290                 295                 300

Lys Pro Ser Ser Pro
305

<210> SEQ ID NO 3
<211> LENGTH: 141
<212> TYPE: DNA
<213> ORGANISM: Rattus norvegicus

<400> SEQUENCE: 3
atggccgctg ttacctatcc ttcatccgtg cctacgacct tggaccctgg gaatgcatcc      60
tcagcctggc ccctggacac gtccctgggg aatgcatctg ctggcactag cctggcagga     120
ctggctgtca gtggcgaatt c                                                141
```

-continued

<210> SEQ ID NO 4
<211> LENGTH: 45
<212> TYPE: DNA
<213> ORGANISM: herpes simplex virus

<400> SEQUENCE: 4
tgcggccgcc agcctgaact cgctcctgaa gacccggaag attaa                45

<210> SEQ ID NO 5
<211> LENGTH: 1113
<212> TYPE: DNA
<213> ORGANISM: Artificial Sequence
<220> FEATURE:
<223> OTHER INFORMATION: construct includes human TASR44 receptor coding
      sequence in the following order: RSS Tag::hTAS2R16::HSV Tag
<220> FEATURE:
<221> NAME/KEY: CDS
<222> LOCATION: (1)..(1113)

<400> SEQUENCE: 5

```
atg gcc gct gtt acc tat cct tca tcc gtg cct acg acc ttg gac cct       48
Met Ala Ala Val Thr Tyr Pro Ser Ser Val Pro Thr Thr Leu Asp Pro
1               5                   10                  15 ggg aat gca tcc tca gcc tgg ccc ctg gac acg tcc ctg ggg aat gca       96
Gly Asn Ala Ser Ser Ala Trp Pro Leu Asp Thr Ser Leu Gly Asn Ala
            20                  25                  30 tct gct ggc act agc ctg gca gga ctg gct gtc agt ggc gaa ttc atg      144
Ser Ala Gly Thr Ser Leu Ala Gly Leu Ala Val Ser Gly Glu Phe Met
        35                  40                  45 aca act ttt ata ccc atc att ttt tcc agt gtg gta gtg gtt cta ttt      192
Thr Thr Phe Ile Pro Ile Ile Phe Ser Ser Val Val Val Val Leu Phe
    50                  55                  60 gtt att gga aat ttt gct aat ggc ttc ata gca ttg gta aat tcc att      240
Val Ile Gly Asn Phe Ala Asn Gly Phe Ile Ala Leu Val Asn Ser Ile
65                  70                  75                  80 gag cgg gtc aag aga caa aag atc tct ttt gct gac cag att ctc act      288
Glu Arg Val Lys Arg Gln Lys Ile Ser Phe Ala Asp Gln Ile Leu Thr
                85                  90                  95 gct ctg gcg gtc tcc aga gtt ggt ttg ctc tgg gta tta tta aat         336
Ala Leu Ala Val Ser Arg Val Gly Leu Leu Trp Val Leu Leu Leu Asn
            100                 105                 110 tgg tat tca act gtg ttt aat cca gct ttt tat agt gta gaa gta aga      384
Trp Tyr Ser Thr Val Phe Asn Pro Ala Phe Tyr Ser Val Glu Val Arg
        115                 120                 125 act act gct tat aat gtc tgg gca gta acc ggc cat ttc agc aac tgg      432
Thr Thr Ala Tyr Asn Val Trp Ala Val Thr Gly His Phe Ser Asn Trp
    130                 135                 140 ctt gct act agc ctc agc ata ttt tat ttg ctc aag att gcc aat ttc      480
Leu Ala Thr Ser Leu Ser Ile Phe Tyr Leu Leu Lys Ile Ala Asn Phe
145                 150                 155                 160 tcc aac ctt att ttt ctt cac tta aag agg aga gtt aag agt gtc att      528
Ser Asn Leu Ile Phe Leu His Leu Lys Arg Arg Val Lys Ser Val Ile
                165                 170                 175 ctg gtg atg ctg ttg ggg cct tta cta ttt ttg gct tgt caa ctt ttt      576
Leu Val Met Leu Leu Gly Pro Leu Leu Phe Leu Ala Cys Gln Leu Phe
            180                 185                 190 gtg ata aac atg aaa gag att gta cgg aca aaa gaa tat gaa gga aac      624
Val Ile Asn Met Lys Glu Ile Val Arg Thr Lys Glu Tyr Glu Gly Asn
        195                 200                 205 atg act tgg aag atc aaa ttg agg agt gca gtg tac ctt tca gat gcg      672
Met Thr Trp Lys Ile Lys Leu Arg Ser Ala Val Tyr Leu Ser Asp Ala
    210                 215                 220
```

```
act gta acc acg cta gga aac tta gtg ccc ttc act ctg acc ctg cta        720
Thr Val Thr Thr Leu Gly Asn Leu Val Pro Phe Thr Leu Thr Leu Leu
225                 230                 235                 240 tgt ttt ttg ctg tta atc tgt tct ctg tgt aaa cat ctc aag aag atg        768
Cys Phe Leu Leu Leu Ile Cys Ser Leu Cys Lys His Leu Lys Lys Met
            245                 250                 255 cag ctc cat ggt aaa gga tct caa gat ccc agc acc aag gtc cac ata        816
Gln Leu His Gly Lys Gly Ser Gln Asp Pro Ser Thr Lys Val His Ile
        260                 265                 270 aaa gct ttg caa act gtg atc ttt ttc ctc ttg tta tgt gcc gtt tac        864
Lys Ala Leu Gln Thr Val Ile Phe Phe Leu Leu Leu Cys Ala Val Tyr
    275                 280                 285 ttt ctg tcc ata atg ata tca gtt tgg agt ttt ggg agt ctg gaa aac        912
Phe Leu Ser Ile Met Ile Ser Val Trp Ser Phe Gly Ser Leu Glu Asn
290                 295                 300 aaa cct gtc ttc atg ttc tgc aaa gct att aga ttc agc tat cct tca        960
Lys Pro Val Phe Met Phe Cys Lys Ala Ile Arg Phe Ser Tyr Pro Ser
305                 310                 315                 320 atc cac cca ttc atc ctg att tgg gga aac aag aag cta aag cag act       1008
Ile His Pro Phe Ile Leu Ile Trp Gly Asn Lys Lys Leu Lys Gln Thr
            325                 330                 335 ttt ctt tca gtt ttg cgg caa gtg agg tac tgg gtg aaa gga gag aag       1056
Phe Leu Ser Val Leu Arg Gln Val Arg Tyr Trp Val Lys Gly Glu Lys
        340                 345                 350 cct tca tct cca tgc ggc cgc cag cct gaa ctc gct cct gaa gac ccg       1104
Pro Ser Ser Pro Cys Gly Arg Gln Pro Glu Leu Ala Pro Glu Asp Pro
    355                 360                 365 gaa gat taa                                                            1113
Glu Asp
    370

<210> SEQ ID NO 6
<211> LENGTH: 370
<212> TYPE: PRT
<213> ORGANISM: Artificial Sequence
<220> FEATURE:
<223> OTHER INFORMATION: Synthetic Construct

<400> SEQUENCE: 6

Met Ala Ala Val Thr Tyr Pro Ser Ser Val Pro Thr Thr Leu Asp Pro
1               5                   10                  15

Gly Asn Ala Ser Ser Ala Trp Pro Leu Asp Thr Ser Leu Gly Asn Ala
            20                  25                  30

Ser Ala Gly Thr Ser Leu Ala Gly Leu Ala Val Ser Gly Glu Phe Met
        35                  40                  45

Thr Thr Phe Ile Pro Ile Phe Ser Ser Val Val Val Leu Phe
    50                  55                  60

Val Ile Gly Asn Phe Ala Asn Gly Phe Ile Ala Leu Val Asn Ser Ile
65                  70                  75                  80

Glu Arg Val Lys Arg Gln Lys Ile Ser Phe Ala Asp Gln Ile Leu Thr
            85                  90                  95

Ala Leu Ala Val Ser Arg Val Gly Leu Leu Trp Val Leu Leu Leu Asn
        100                 105                 110

Trp Tyr Ser Thr Val Phe Asn Pro Ala Phe Tyr Ser Val Glu Val Arg
    115                 120                 125

Thr Thr Ala Tyr Asn Val Trp Ala Val Thr Gly His Phe Ser Asn Trp
130                 135                 140

Leu Ala Thr Ser Leu Ser Ile Phe Tyr Leu Leu Lys Ile Ala Asn Phe
145                 150                 155                 160
```

```
Ser Asn Leu Ile Phe Leu His Leu Lys Arg Arg Val Lys Ser Val Ile
            165                 170                 175

Leu Val Met Leu Leu Gly Pro Leu Leu Phe Leu Ala Cys Gln Leu Phe
            180                 185                 190

Val Ile Asn Met Lys Glu Ile Val Arg Thr Lys Glu Tyr Glu Gly Asn
            195                 200                 205

Met Thr Trp Lys Ile Lys Leu Arg Ser Ala Val Tyr Leu Ser Asp Ala
            210                 215                 220

Thr Val Thr Thr Leu Gly Asn Leu Val Pro Phe Thr Leu Thr Leu Leu
225                 230                 235                 240

Cys Phe Leu Leu Leu Ile Cys Ser Leu Cys Lys His Leu Lys Lys Met
            245                 250                 255

Gln Leu His Gly Lys Gly Ser Gln Asp Pro Ser Thr Lys Val His Ile
            260                 265                 270

Lys Ala Leu Gln Thr Val Ile Phe Phe Leu Leu Leu Cys Ala Val Tyr
            275                 280                 285

Phe Leu Ser Ile Met Ile Ser Val Trp Ser Phe Gly Ser Leu Glu Asn
            290                 295                 300

Lys Pro Val Phe Met Phe Cys Lys Ala Ile Arg Phe Ser Tyr Pro Ser
305                 310                 315                 320

Ile His Pro Phe Ile Leu Ile Trp Gly Asn Lys Lys Leu Lys Gln Thr
            325                 330                 335

Phe Leu Ser Val Leu Arg Gln Val Arg Tyr Trp Val Lys Gly Glu Lys
            340                 345                 350

Pro Ser Ser Pro Cys Gly Arg Gln Pro Glu Leu Ala Pro Glu Asp Pro
            355                 360                 365

Glu Asp
    370
```